US006321391B1

(12) United States Patent
Basso

(10) Patent No.: US 6,321,391 B1
(45) Date of Patent: Nov. 27, 2001

(54) GOGGLES AND STRAP COMBINATION

(76) Inventor: Rudolph B. Basso, 461 Underhill La., Charlottesville, VA (US) 22911

( * ) Notice: Subject to any disclaimer, the term of this patent is extended or adjusted under 35 U.S.C. 154(b) by 0 days.

(21) Appl. No.: 09/347,792

(22) Filed: Jul. 6, 1999

Related U.S. Application Data

(60) Provisional application No. 60/091,760, filed on Jul. 6, 1998.

(51) Int. Cl.[7] .......................................................... A61F 9/02
(52) U.S. Cl. .................................. 2/452; 2/445; 128/858
(58) Field of Search ................................ 2/426, 431, 445, 2/454, 452, 9; 351/156, 157; 128/857, 858, 201.12, 201.15, 201.22–201.24, 201.27–201.28, 206.19, 206.21, 206.23, 206.28, 207.11

(56) References Cited

U.S. PATENT DOCUMENTS

| | | | |
|---|---|---|---|
| 5,303,428 | * | 4/1994 | Pernicka .................................... 2/452 |
| 5,429,683 | * | 7/1995 | Le Mitouard ................... 128/206.24 |
| 5,524,300 | * | 6/1996 | Chiang ..................................... 2/439 |
| 5,570,705 | * | 11/1996 | Burke ................................... 128/869 |
| 5,706,526 | * | 1/1998 | Huang ........................................ 2/42 |
| 5,711,036 | * | 1/1998 | Kita et al. ................................ 2/428 |
| 5,857,221 | * | 1/1999 | Geneve et al. ........................... 2/428 |
| 5,887,587 | * | 3/1999 | Groenke .......................... 128/207.13 |

\* cited by examiner

Primary Examiner—John J. Calvert
Assistant Examiner—Katherine Moran
(74) Attorney, Agent, or Firm—Sheldon H. Parker

(57) ABSTRACT

A modified sport or work goggles, includes a first and second top strap, a first and second bottom strap, a first and a second goggles lens, and a bridge. The first and second goggles lenses are attached through the bridge and the first top and first bottom straps are opposedly attached to the first goggles lens and the second top and second bottom straps are opposedly attached to the second goggles lens. The top straps extend from said goggles at an angle in the range from about 35 to about 90 degrees relative to the longitudinal line of said goggles, and the bottom straps form an acute angle with respect to the longitudinal line of the goggles, in the range from about 15 to about 70°.

7 Claims, 28 Drawing Sheets

GOGGLES AND STRAP COMBINATION

CROSS-REFERENCE TO RELATED APPLICATION

This application claims the benefit of copending provisional patent application 60/091,760, filed Jul. 6, 1998, titled Goggles and Strap Combination, the disclosure of which is incorporated herein by reference, as though recited in full.

BACKGROUND OF THE INVENTION

1. Field of the Invention

The disclosed invention relates to an improved sport or work goggles and strap combination, which will not angle, tip or move from the user's eyes.

2. Brief Description of the Prior Art

Goggles are used in various sports, as well as the workplace, to protect the user's eyes. Maintaining the goggles in position have always been a problem when any pressure, such as diving, is applied to the goggles. Users experience the problem of goggles being flipped out of position in use, as for example, during entry to a swimming pool during a swimming meet.

SUMMARY OF THE INVENTION

The disclosed goggle/strap combination overcomes the problem of maintaining the goggles in position by connecting the strap at the top and bottom of the goggles. This connection places the strap over and around the user's head, preventing the goggles from sliding, lifting or flipping during use. The most severe problem being the rotation of the goggles about the longitudinal axis of the goggles The invention relates to a novel method of maintaining goggles in position during use. The straps are connected to the goggles at the top and bottom of the eyepieces rather than at the sides. In one embodiment the straps are crossed over to form an X at the back of the user's head. In other embodiments, a bottom strap extends around the back of the user's head and various configurations of top and connecting straps connect the bottom strap to the top of the goggles.

Unless otherwise specified, the terms used herein, are employed in accordance with their standard dictionary definition, in particular, the American Heritage Dictionary, Third Edition, Version 3.6, copyright 1994.

The term "opposed", as employed herein, pertains to how the top and bottom straps are attached, with respect to one another, to the goggles lens or goggles lens template. As used herein, opposed or opposedly is intended to mean that the straps that are attached to the goggles lens or goggles lens template in sufficient counterbalance to one another so that the top strap prevents the lens from rolling or sliding off of the eye during normal or increased pressure (e.g., diving) and the bottom strap maintains the goggles secure to the face by countering the force of the top strap. The top and bottom straps are at an angle to a line through the longitudinal line of the goggles. The longitudinal line should be understood to be the straight line running from outermost edges of the goggles, and through the lenses of the goggles. With respect to a person that is standing upright, the longitudinal line would be horizontal relative to the vertical position of the person. Conventional, or prior art goggles, typically have end strap receiving slots which extend perpendicularly to the longitudinal line of the goggles.

The top straps preferably extend from the goggles at an angle in the range from about 35 to about 90 degrees. More preferably, the top straps extend away from each other and form an angle relative to the longitudinal line of the goggles, in the range from about 45 to about 75°.

The bottom straps oppose the top straps, and it appears that the action of the lower right straps opposes the force of the top left strap, and the lower left strap opposes the top right strap. Thus, the bottom straps can form an acute angle with respect to the longitudinal line of the goggles. The preferred angle is in the range from about 15 to about 70°, and more preferably in the range from about 20 to about 35°.

Straps, as used herein, are intended to refer to straps used to secure goggles to the wearer. The straps can be comprised of materials known to those of skill in the art to be useful for the arena in which the goggles are to be worn (e.g., swimming). The straps can be of different lengths, widths, colors, and materials depending on the desired characteristics of the goggle. Typical material are synthetic polymers, such as silicones, urethanes, and synthetic rubbers. The straps can be directly attached to the goggles lens or goggle lens template via a chemical bond (i.e., glue, heat, or epoxy) or a mechanical bond (e.g., a clamp, hinge, thread, nut and bolt, or crimping device) or they can be continuous with the goggles lens template. In order to allow for adjustment of the goggle, the straps can be made adjustable by looping the strap through a receiving slot (e.g., a receiving slot in the goggles lens, goggles lens template, or interface) and securing the loop via a clip, knot, clamp, crimping device, or other securing device known to those of skill in the art. If desired, the straps can be attached to the goggles lens, goggles lens template, or interface without an adjusting loop. The straps can also be adjusted through the use of the presently described interface with or without the presence of a loop. A securing means such as a clamp, clip, slide, nut and bolt, knot, or crimpable device, can be present on the side of the interface opposite the back of the skull which can be used to adjust the fit of the goggle.

A sport or work goggle, as used herein, is intended to refer to an apparatus designed to cover the wearer's eyes and protect them from their environment (e.g., chlorinated water or flying dust). The sport or work goggle, comprises: a first and second central or longitudinal strap, a first and second goggles lens, and a bridge connect the lenses.

A modified sport or work goggles, as used herein, preferably, comprises: first and second top straps, first and second bottom straps, first and second goggles lenses and a bridge, wherein the first and second goggleslenses are attached through the bridge and the first top and first bottom straps are opposedly attached to the first goggleslens and the second top and second bottom straps are opposedly attached to the second goggleslens. Optionally, the modified goggles-further comprises: first and second center straps. The center straps are attached to the goggleslenses between the top and bottom straps. Preferably, the center straps are present.

The first and second top and bottom straps are opposedly attached to the goggleslenses. The first and second top and bottom straps can be attached to the goggleslens template via a chemical bond (i.e., glue, heat, or epoxy) or a mechanical bond (e.g., a clamp, hinge, thread, nut and bolt, staple, or crimping device) or they can be continuous with the goggleslens template. If a chemical or mechanical means is used, then the straps can be looped through a receiving slot in the template and secured by a securing means described above to allow for adjustment, or they can be directly attached to the goggleslens template. The straps can be continuous such that the first top strap is connected with the second bottom strap and the second top strap is connected with the first bottom strap. If present, the center straps can also be continuous. The continuous top and bottom straps criss-cross in the back of the wearer's head to form an X. An interface can be used with the continuous straps to allow for adjustment. Each strap passes through two receiving slots depending on whether or not the center straps are present. The continuous straps can be adjusted via a loop around a receiving slot in the goggleslenses. In addition to or alternatively, the continuous straps can be adjusted using a securing means as described above which prevents the strap from passing back through the interface. Preferably a securing means such as a clamp, clip, slide, nut and bolt, knot, or crimpable device is used.

Preferably, the straps are not continuous (i.e., there are four individual non-connected straps). In this instance, an interface can be used to secure the straps to the back of the wearer's head. The four straps are passed through receiving slots in the interface. Preferably, the center straps are present and all six straps are passed through receiving slots in the interface. The straps can then be adjusted using a loop as described above or a securing means which prevents the strap from passing back through the interface. Preferably a securing means such as a clamp, clip, slide, nut and bolt, knot, or crimpable device is used and is located on the side of the interface opposite of the goggleslens template.

The term "overlay", as used herein, is intended to mean an apparatus designed to fit over an existing sport or work goggles (e.g., swimming, diving, or laboratory). The intent of the overlay is to convert goggles which contains central straps to goggles which contains top and bottom straps and optional central straps. Preferably, the overlay creates goggles with top, central, and bottom straps.

The overlay of the present invention preferably comprises: first and second top straps, first and second bottom straps, and a goggleslens template. The goggleslens template, comprises: first and second goggleslens rings and a bridge and is designed to circumscribe the lens of a selected gogglesthrough the first and second goggleslens rings. The dimensions of these rings will depend on the dimensions of the gogglesdesired to be modified. It is desirable that the goggles lens rings circumscribe the goggles lens in a manner which limits any interference with the original sight of the goggles wearer. The goggles lens rings are attached through the bridge. The bridge separates the goggles lens rings so that the template fits the selected goggles. Preferably, the goggles lens template is one continuous piece. The template can be comprised of material like that used for the straps.

As indicated above, the straps are oppposedly attached to the goggles lens template. The first and second top and bottom straps can be attached to the goggles lens template via a chemical bond (i.e., glue, heat, or epoxy) or a mechanical bond (e.g., a clamp, hinge, thread, nut and bolt, staple, or crimping device) or they can be continuous with the goggles lens template. If a chemical or mechanical means is used, then the straps can be looped through a receiving slot in the template and secured by a securing means described above to allow for adjustment, or they can be directly attached to the goggles lens template.

The straps of the overlay can be continuous such that the first top strap is connected with the second bottom strap and the second top strap is connected with the first bottom strap. The continuous straps criss-cross in the back of the wearer's head to form an X. An interface can be used with continuous straps to allow for adjustment. Each strap passes through two receiving slots in the interface and form an X thereon.

The continuous straps can be adjusted via a loop around a receiving slot in the goggles lens rings. In addition to or alternatively, the continuous straps can be adjusted using a securing means as described above which prevents the strap from passing back through the interface. Preferably a securing means such as a clamp, clip, slide, nut and bolt, knot, or crimpable device is used.

Preferably, the straps of the overlay are not continuous (i.e., there are four individual non-connected straps). In this instance, an interface can be used to secure the straps to the back of the wearer's head. The four straps are passed through a receiving slot in the interface. The straps can then be adjusted using a loop as described above or a securing means which prevents the strap from passing back through the interface. Preferably a securing means such as a clamp, clip, slide, nut and bolt, knot, or crimpable device is used and is located on the side of the interface opposite of the goggles lens template.

BRIEF DESCRIPTION OF THE DRAWINGS

The advantages of the instant disclosure will become more apparent when read with the specification and drawings, wherein.

DETAILED DESCRIPTION OF THE INVENTION

Goggles are worn in many sports and work activities to protect the user's eyes and increase visibility. In some instances, however, there is a difficulty in maintaining the goggles in the proper position. This is especially true in water sports where the pressure exerted rearward by the water tends to tilt or move the goggles from the user's eyes. To overcome the positioning problems associated with goggles, especially when used in water sports, the disclosed goggles are redesigned to permit the straps to come behind and over the user's head, thereby preventing excessive movement in any direction.

Figure 1:
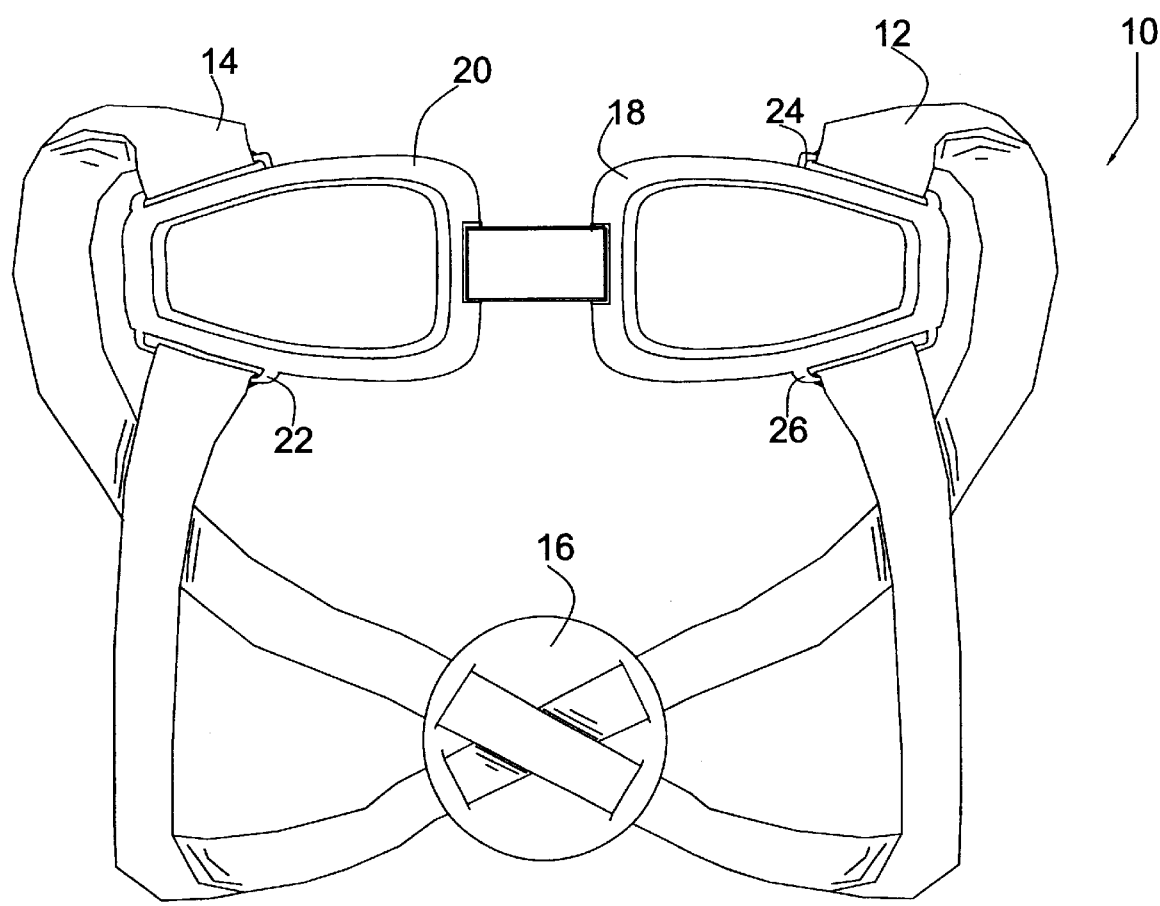
FIG. 1 is a perspective front view of swim goggles using one embodiment of the strapping system.

The goggles 10, as illustrated in FIG. 1 have been designed to receive the straps 12 and 14 at the top and bottom of the goggles 10. The top receiving slots 20 and 24 and bottom receiving slots 22 and 26. Prior art goggles receive a single strap on either side of the goggles, allowing the eyepieces to tip. The placement of the top receiving slots 20 and 24 opposite the bottom receiving slots 22 and 26 enables the opposite pair of straps to maintain the eyepieces 18 and 20 in position.

The strap 12 is connected at the top of the eyepiece 18, loops through the interface 16 and is connected at the bottom of the eyepiece 20. The strap 14 is connected at the top of the eyepiece 20, passes through the interface 16 and is connected at the bottom of the eyepiece 18. The interface 16 illustrated herein has a circular configuration which is slit to allow for the straps 12 and 14 to weave through. Other configurations and attachment means can also be used for the interface and these will be apparent to those skilled in the art. The crossing of the straps 12 and 14 form an X behind the user's head, as can be seen more clearly in FIG. 2, providing a security which was formerly unattainable in goggles. The attachment of the straps 12 and 14 to the top and bottom of the eyepieces 18 and 20 prevents the goggles 10 from tipping. The straps 12 and 14 can be manufactured as either adjustable or unadjustable, depending upon cost, end use and user preference The goggles 30, illustrated in FIG. 3, are a larger, heavy-duty style, which are generally used in scuba diving. The goggles 30 are illustrated using the center top strap 36, in addition to the crossing straps 34 and 32. Although the center top strap 36 is optional, it does provide additional security with the larger and heavier goggles.

FIGS. 4–7, 10–17 and 20–21 illustrate various designs, which do not incorporate the interface as disclosed heretofore. In these embodiments the straps are either molded together at time of manufacture or connected to one another through use of method appropriate for the materials used. Molding is the preferred method of manufacture as the procedure is less expensive.

Figure 4:
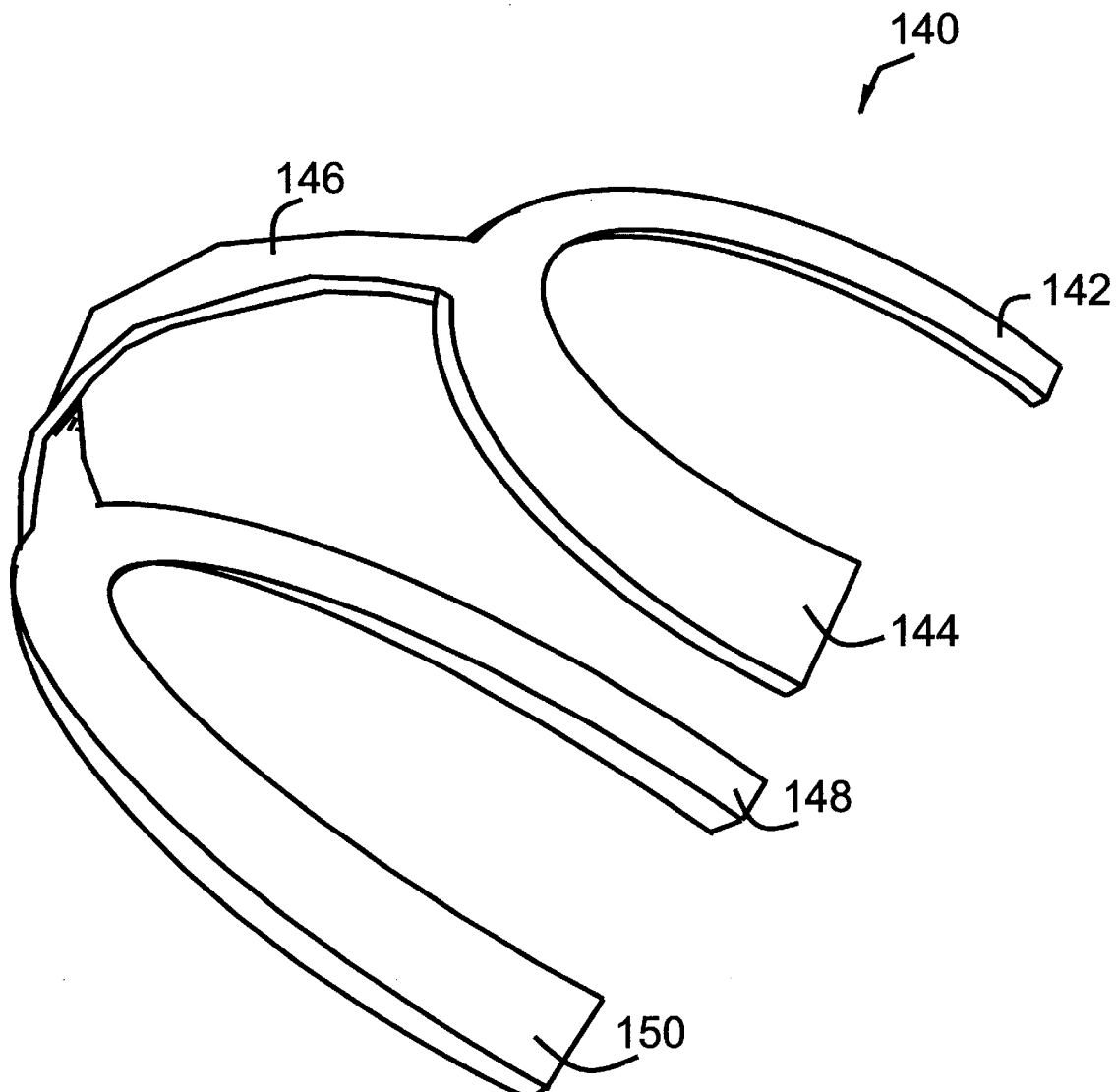
FIG. 4 is a side perspective view of one embodiment of the straps having a dual bottom strap, single connector strap and dual top straps.

In FIG. 4 the top straps 142 and 144 are connected to the bottom straps 148 and 150 through use of a connecting strap 146. Although referred to herein as bottom straps 148 and 150, the bottom strap is preferably one piece. The connecting strap 146 is connected to the bottom straps 148 and 150 at right angles at approximately the center point and then and is then split into top straps 142 and 144. The ends of the top straps 142 and 144 are affixed to the top of the goggles and the ends of the bottom straps 148 and 150 attached to the bottom of the goggles.

Figure 5:
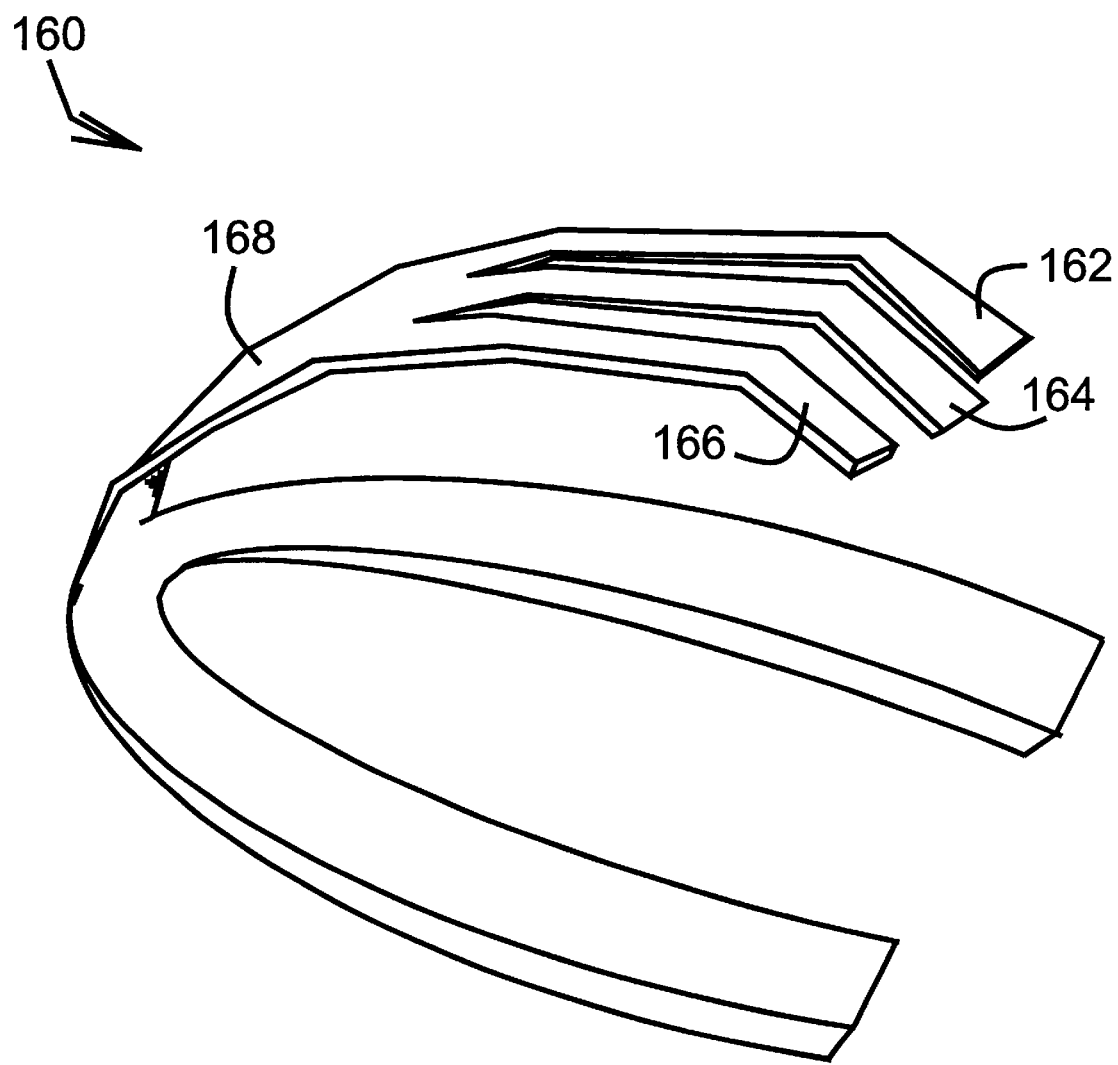
FIG. 5 is a side perspective view of another embodiment of the straps having a dual bottom straps, single connector strap and three top straps.

In FIG. 5 the connecting strap 168 is divided into three pieces to form individual straps 162, 164 and 166. This embodiment would provide a center strap 164 to attach to the middle of a facemask of the type illustrated in FIG. 3. This strap embodiment provides the added security required when using the larger masks. This is especially applicable in water sports such as scuba diving where maintaining the mask in position is increased during entry.

Figure 6:
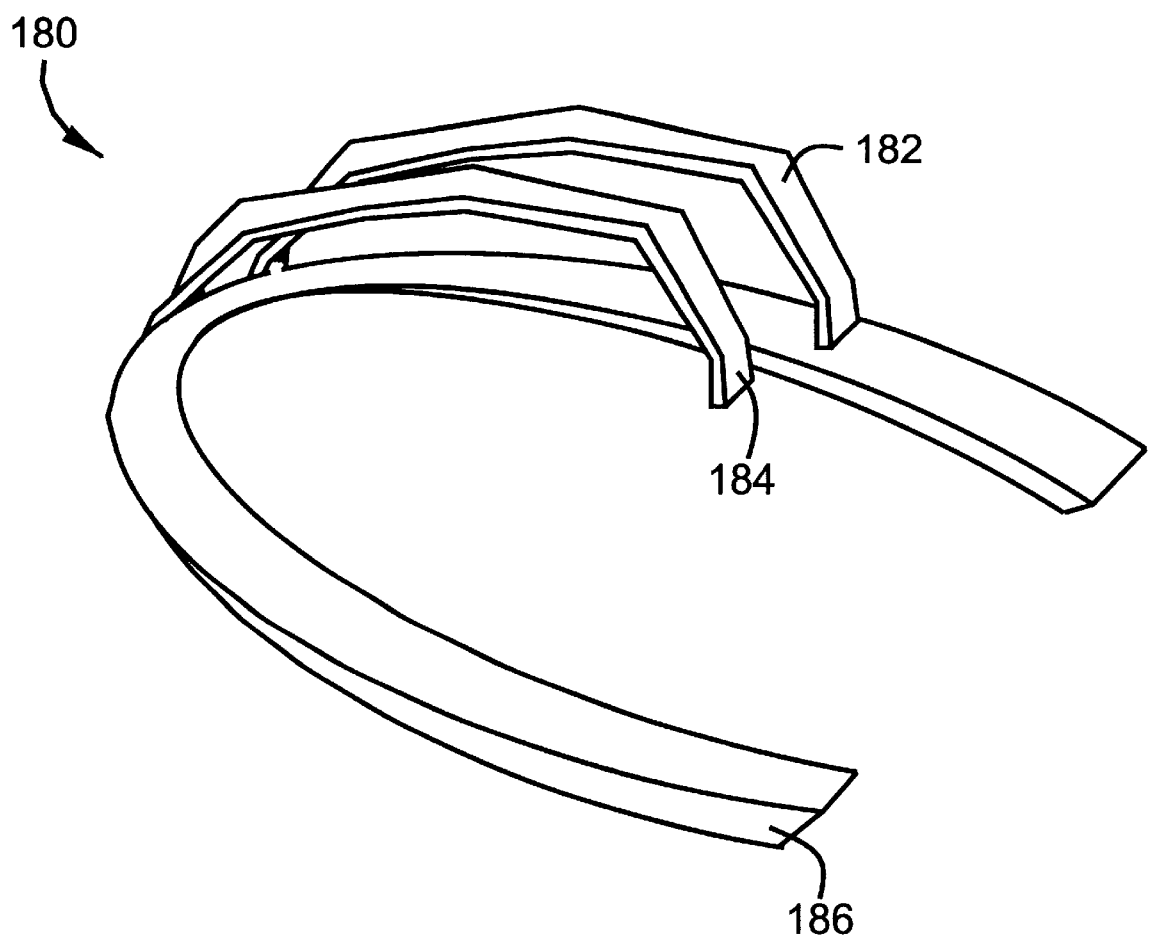
FIG. 6 is a side perspective view of an additional embodiment of the straps having dual bottom straps and dual direct connector straps.

In the embodiment of FIG. 6 two independently top straps 182 and 184 are connected to one end to the bottom strap 186 and at the open end to the goggles.

Figure 7:
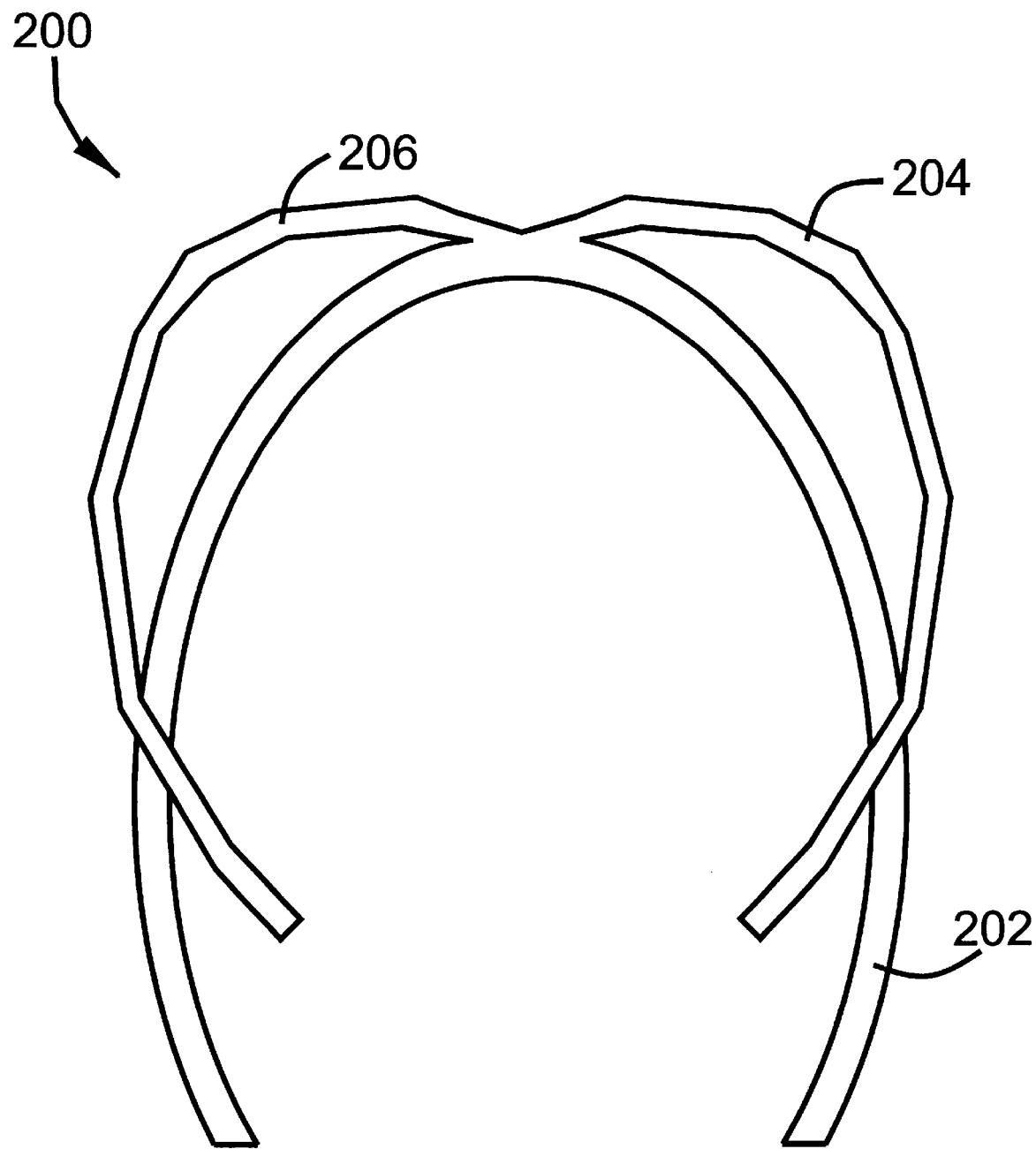
FIG. 7 is a front perspective view of the embodiment of FIG. 6.

The strap system 200 of FIG. 7 uses dual top straps 204 and 206 which extend directly from a single point on the bottom strap 202. As stated heretofore, the bottom strap 202 and top straps 204 and 206 can be individual straps which are adhered to one another or be manufacture from a single piece of material molded to the desired configuration.

Figure 8:
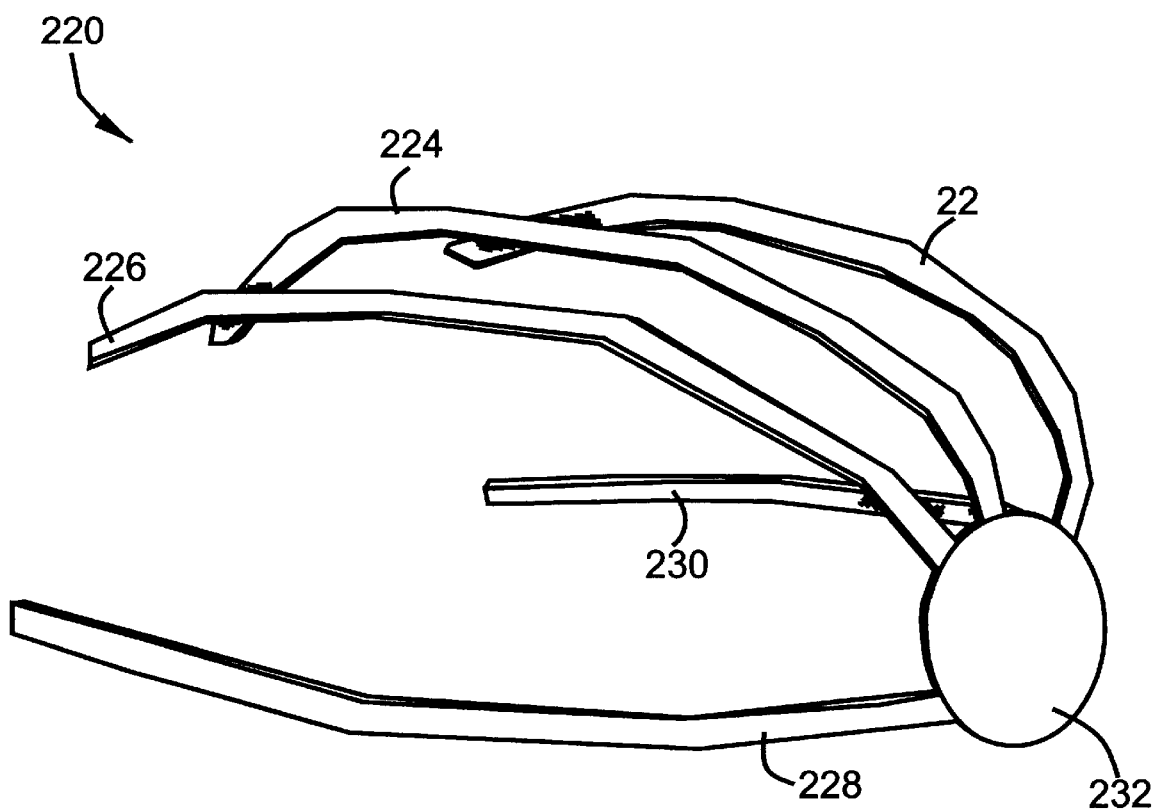
FIG. 8 is a side perspective view of an embodiment having two bottom straps and three direct connector straps joined at an interface.
Figure 9:
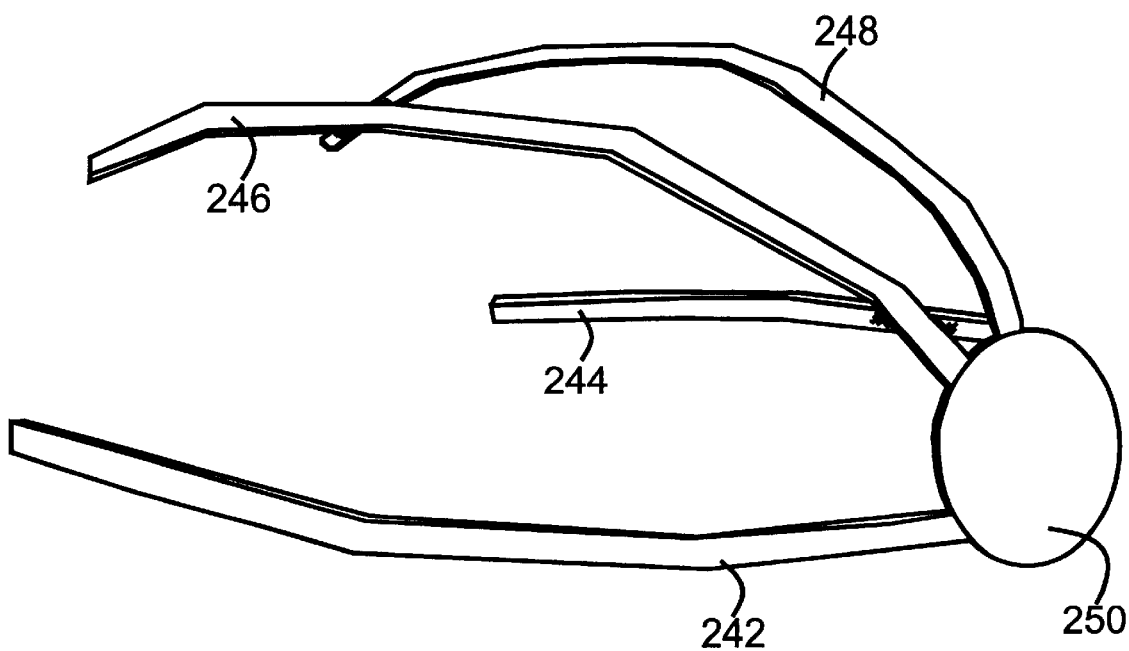
FIG. 9 is a side perspective view of two lower straps and two direct connector straps joined at an interface.

The strap illustrated in FIG. 8 incorporates an interface 232 from which the top straps 222, 224, 226 and bottom straps 228 and 230 protrude. The embodiment illustrated in FIG. 9 is the same basic configuration, however rather than three top straps, the embodiment of FIG. 9 has two top straps 246 and 248. The top straps 246 and 246 are connected to the bottom straps 242 and 244 at the interface 250. In the preferred embodiment the straps and interfaces are molded as one piece rather than straps woven through the interface as disclosed in FIGS. 1–3 and 18.

Figure 10:
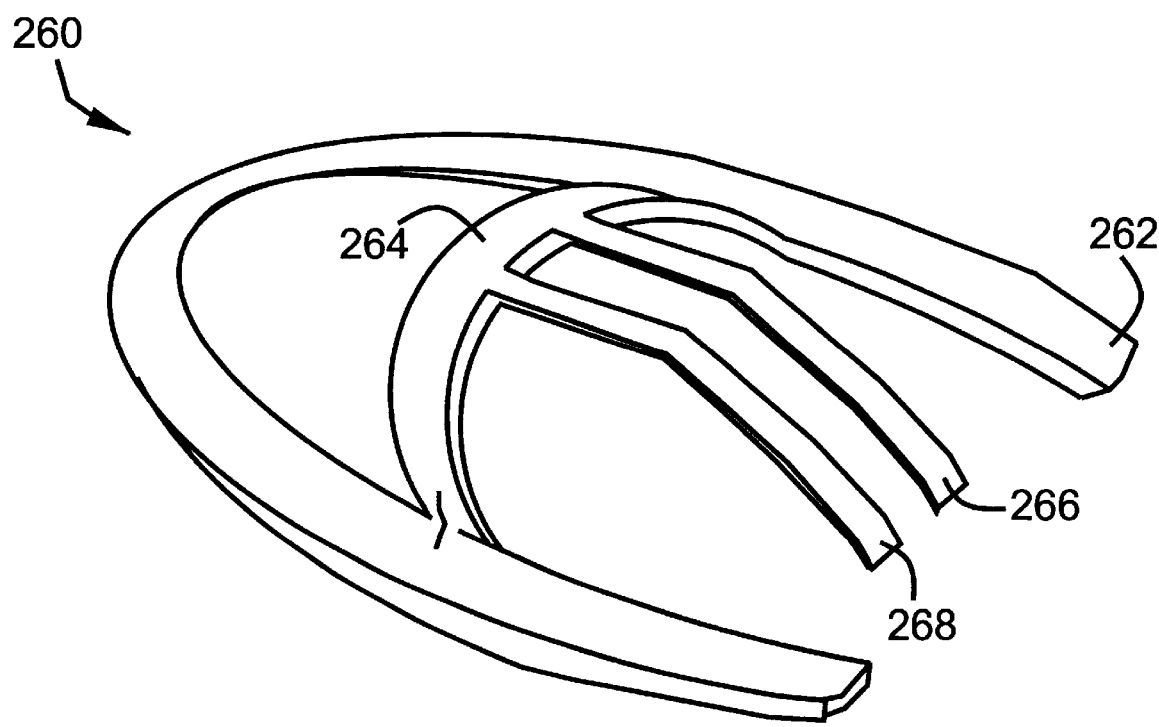
FIG. 10 is a side perspective view of two bottom straps, side to side connector strap and two front straps.
Figure 11:
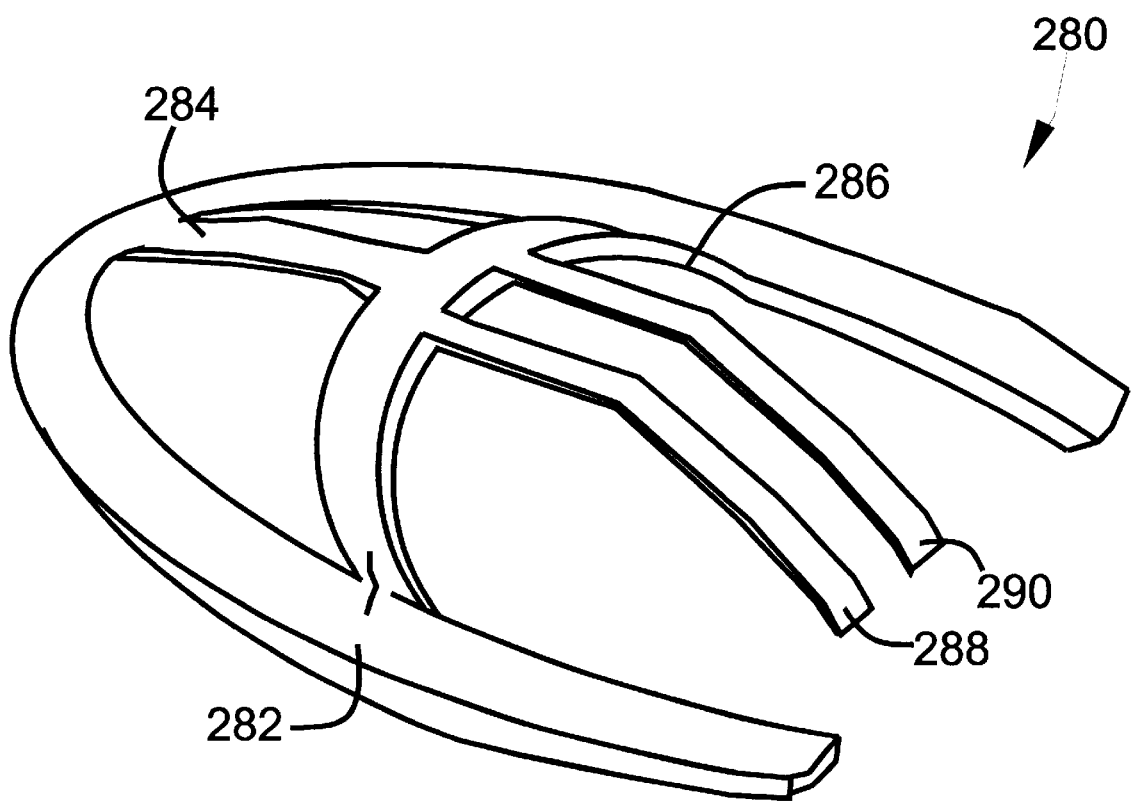
FIG. 11 is a side perspective view of two bottom straps, side to side connector strap, back strap and two front straps.
Figure 12:
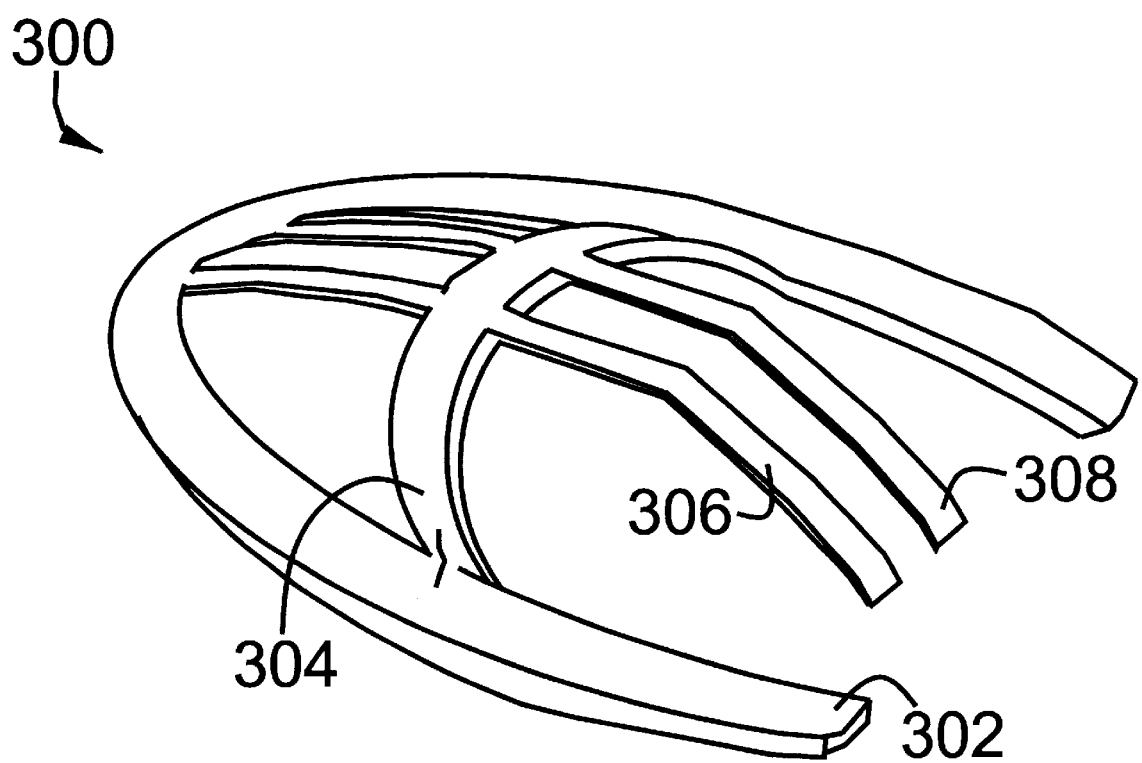
FIG. 12 is a side perspective view of an embodiment incorporating two bottom straps, side to side connector strap and two back to front direct connecting straps.

In FIGS. 10, 11 and 12 a lateral strap had been added to provide additional support. In FIG. 10 the lateral support 264 is affixed to the bottom strap 262. The dual top straps 266 and 268 extend from the lateral support 264 to the goggles. In FIG. 11 a back strap 284 has been added which connects the lateral strap 286 with the bottom strap 282. The top straps 288 and 290 are connected directly to the lateral strap 286. FIG. 12 uses two top straps 306 and 308 that attach the back strap 302 at one end and are open for attachment to the goggles at the opposite end. The top straps 306 and 308 are intersected by the lateral strap 304 which is, in turn, attached to the bottom strap 302.

Figure 2:
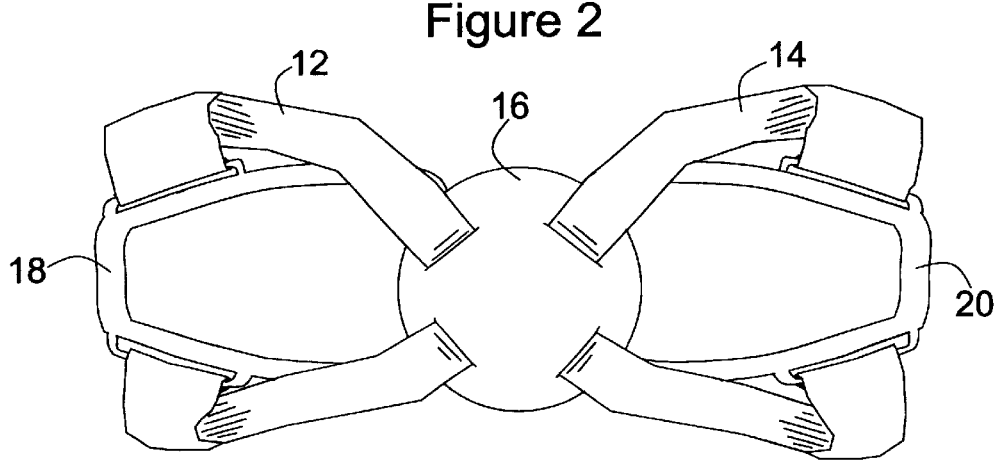
FIG. 2 is a back view of the goggles of FIG. 1.
Figure 3:
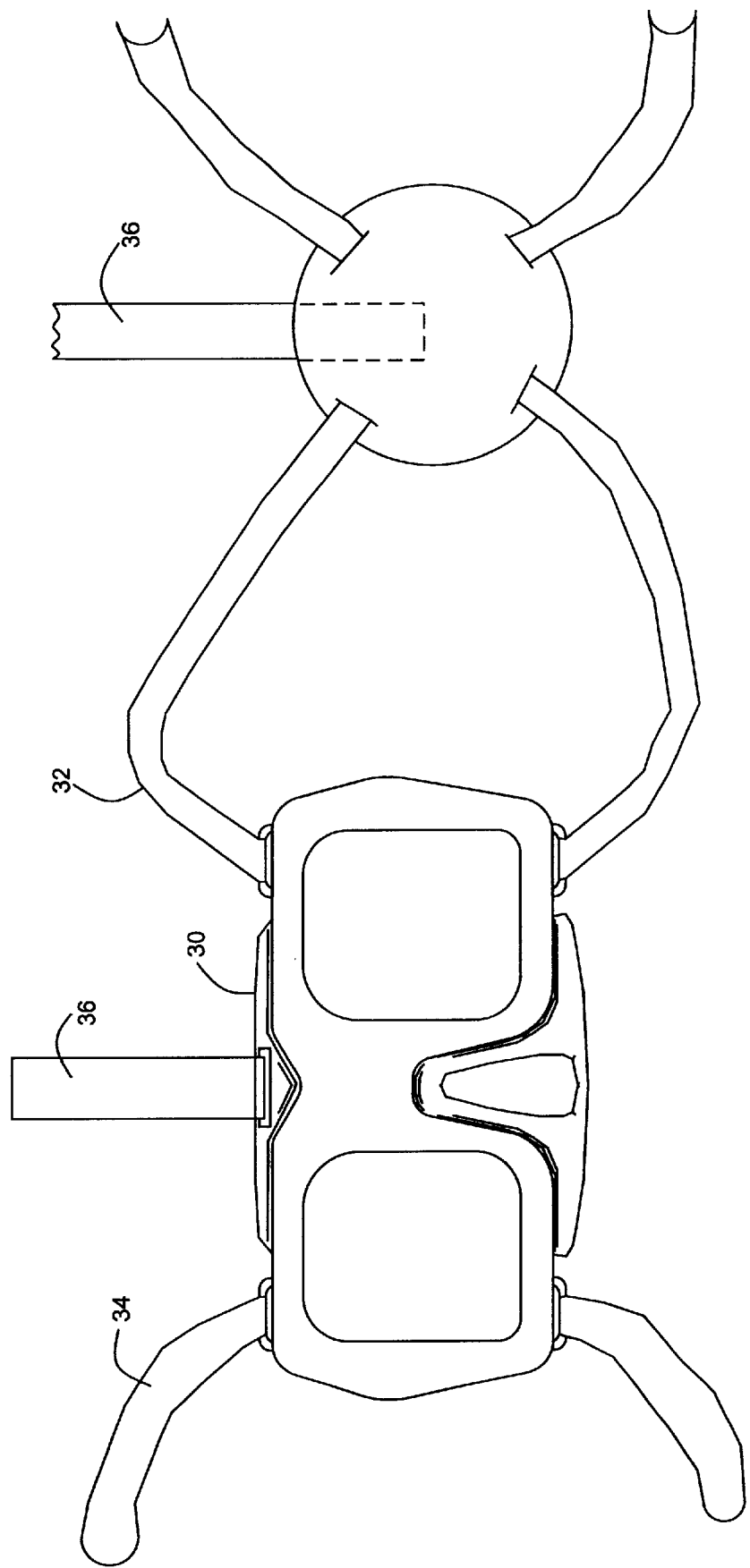
FIG. 3 is a broken view of a traditional dive mask adapted with the improved strapping system.
Figure 13:
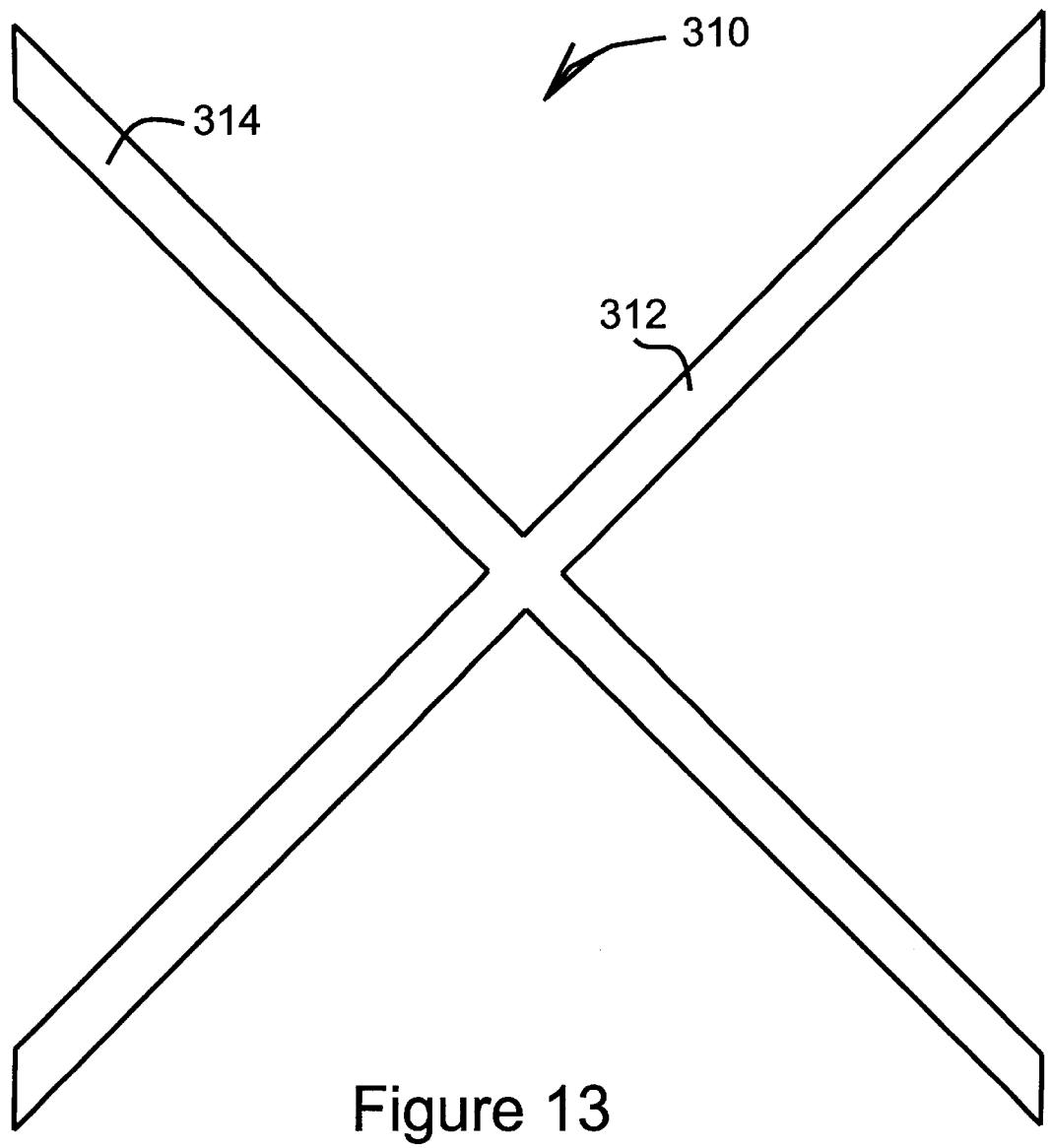
FIG. 13 is a front view of an X connector strap.
Figure 14:
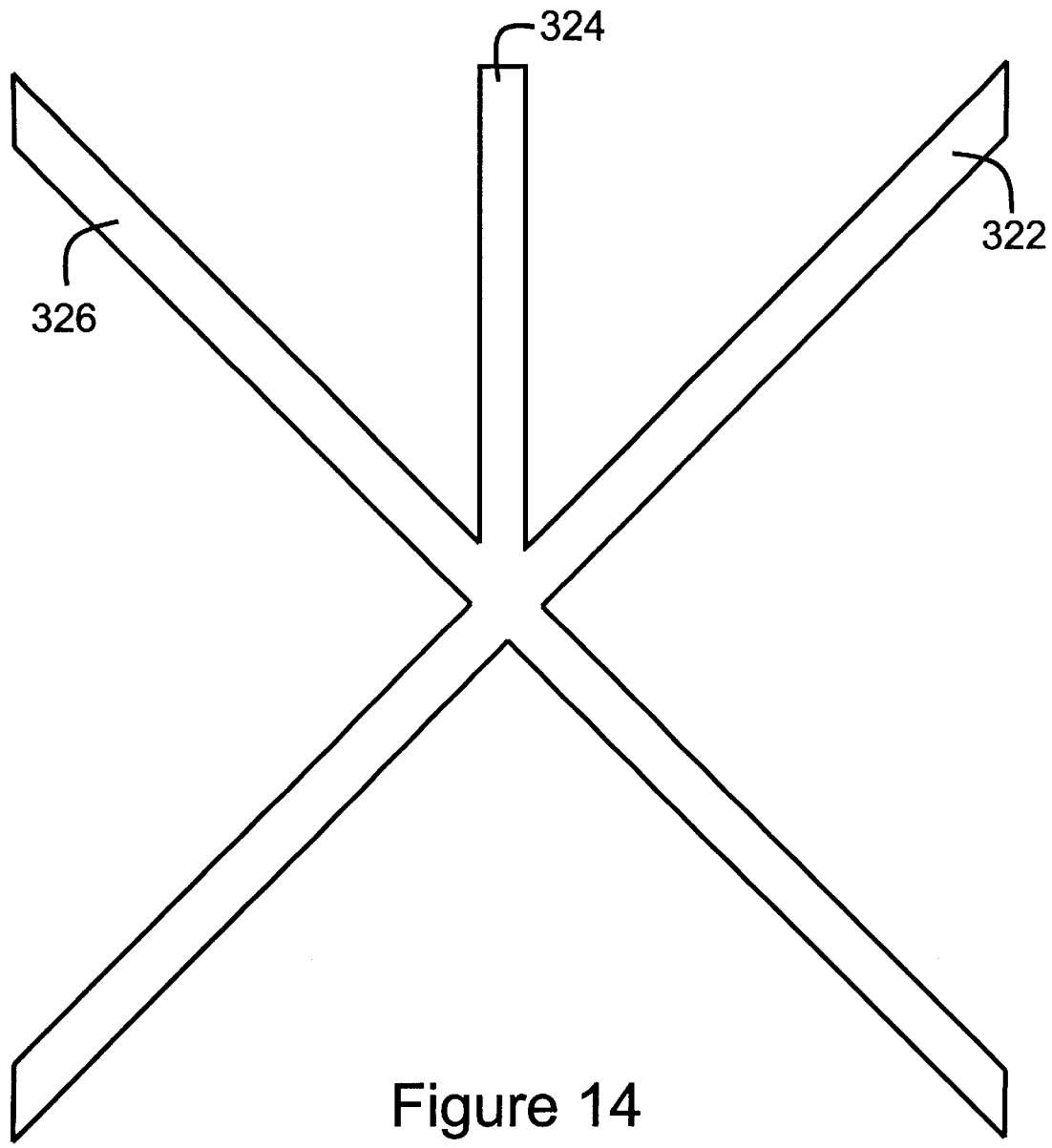
FIG. 14 is a front view of an X connector strap with a third top strap.
Figure 15:
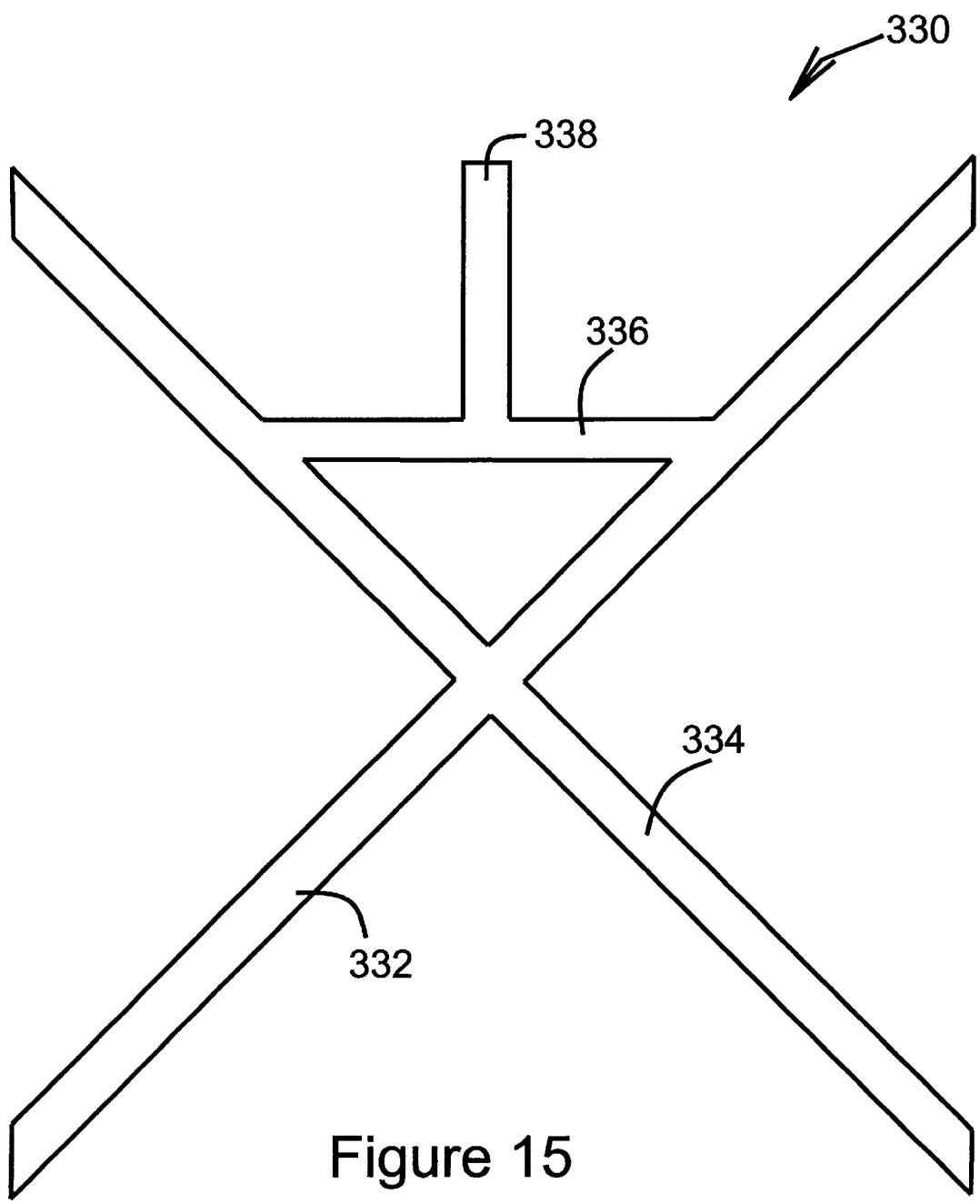
FIG. 15 is a front view of an X connector strap with an inverted T top strap.

The strap designs disclosed in FIGS. 13–17 are variations on the design of an X strap, similar to the design disclosed in FIGS. 1–3. In FIG. 13 the X-strap 310 consists of strap 312 and strap 314 which can either be secured to one another at the cross over point or left loose to provide for user adjustment. In FIG. 14 the X-strap 320 consists of crossing straps 322 and 326 with a center strap 324 affixed to the crossing straps 322 and 326 at the point of overlap. FIG. 15 is a modification of the X-strap 320 of FIG. 14. The crossing straps 332 and 334 are provided with a interface strap 336 with a third top strap 338 forming an inverted T.

Figure 16:
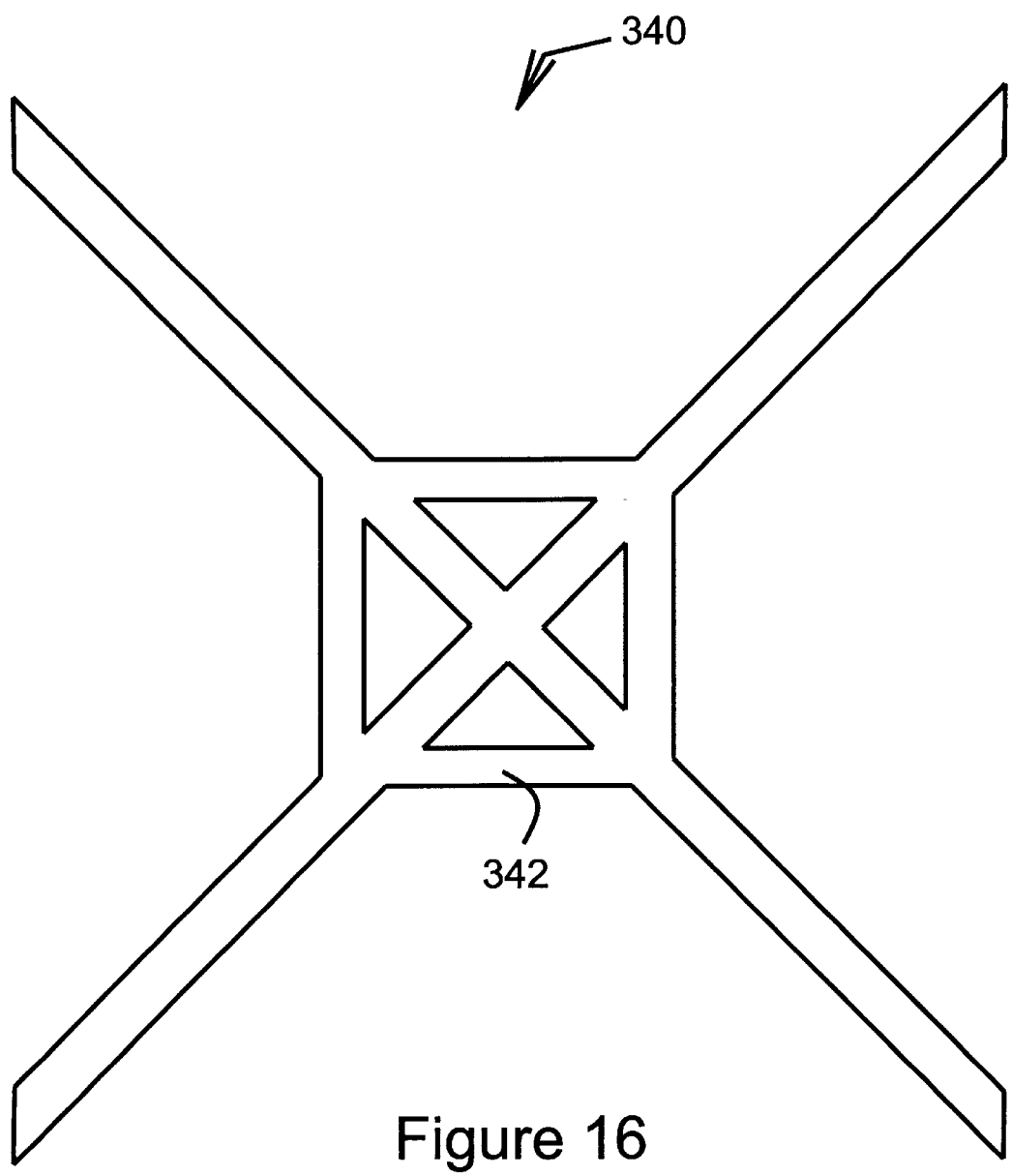
FIG. 16 is a front view of the X connector strap with a square interface.
Figure 17:
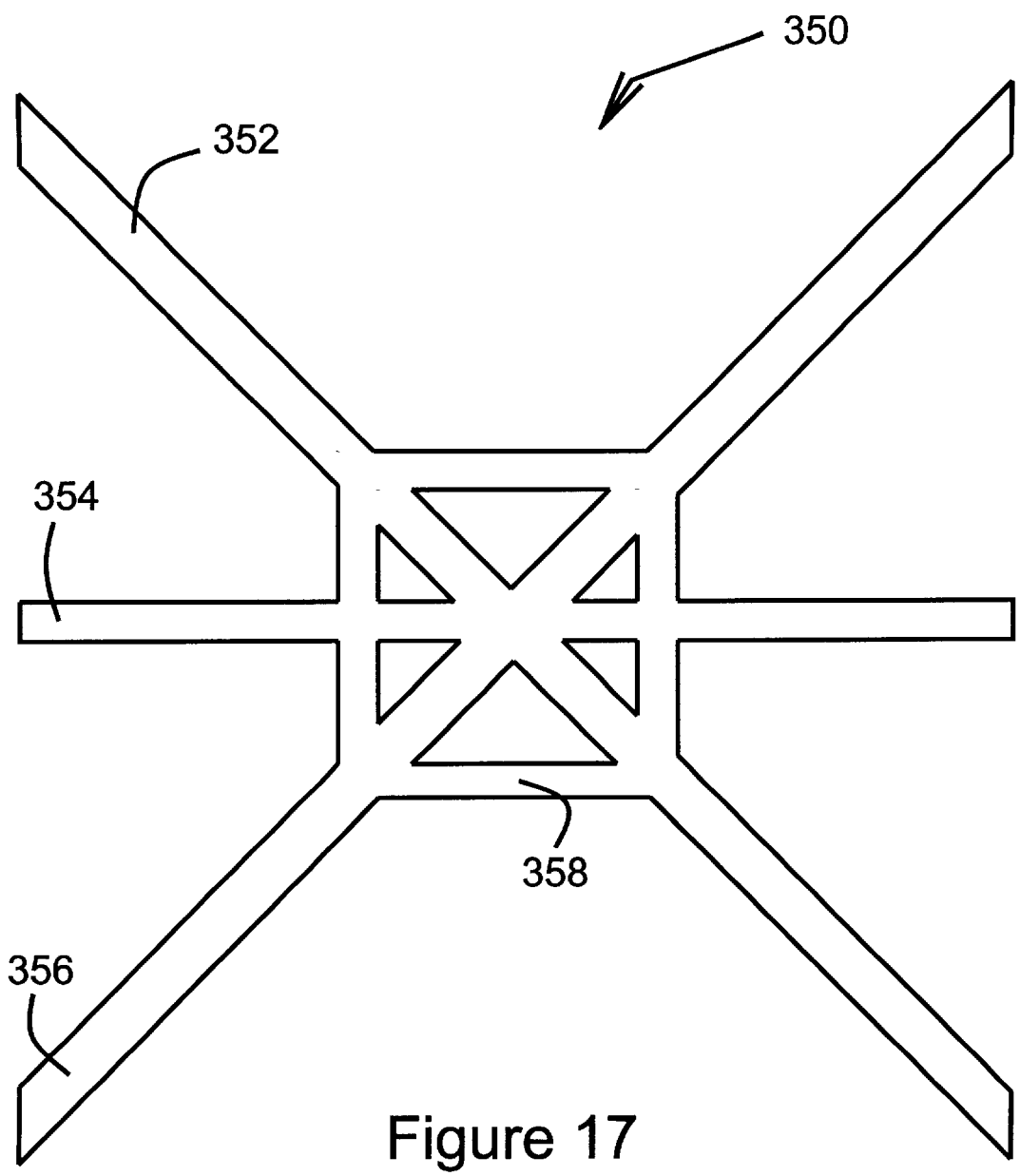
FIG. 17 is a front view of an X connector strap having an addition horizontal side strap, an interface and top straps.
Figure 18:
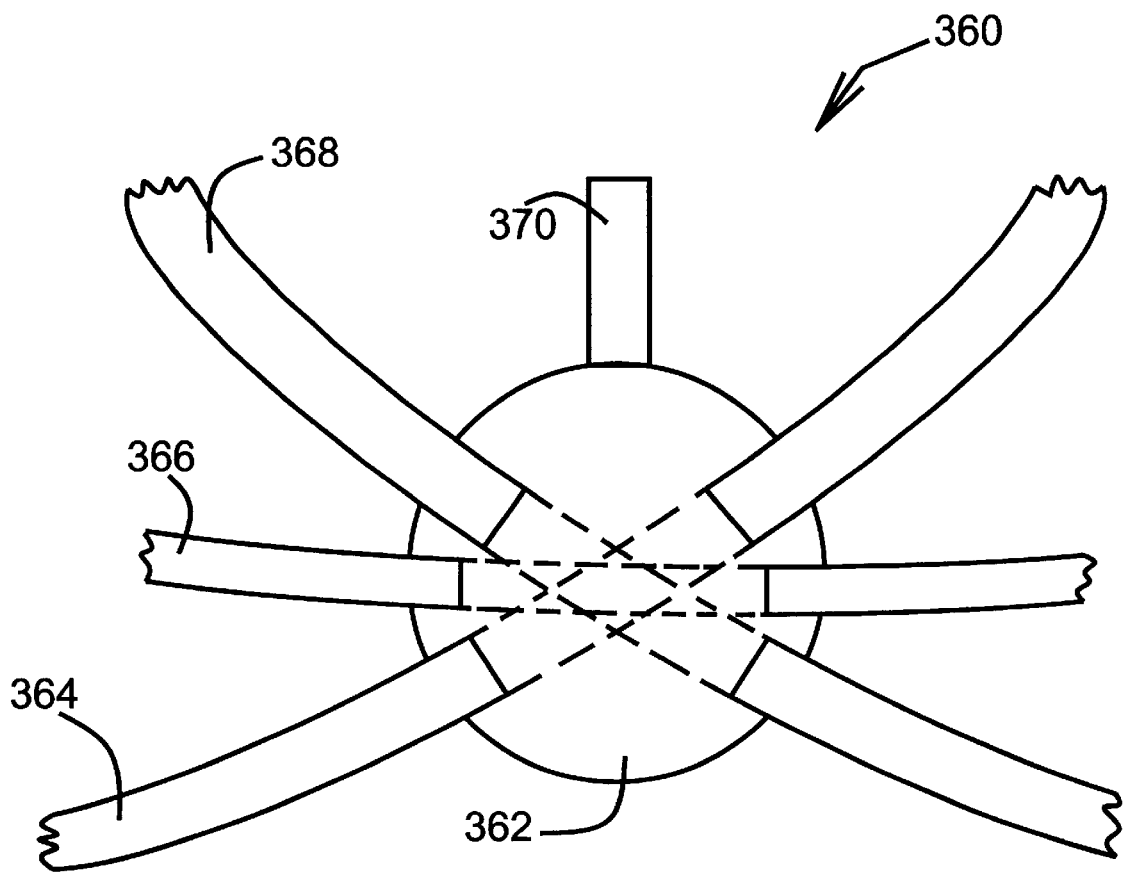
FIG. 18 is a multi strap connector using an interface.
Figure 19:
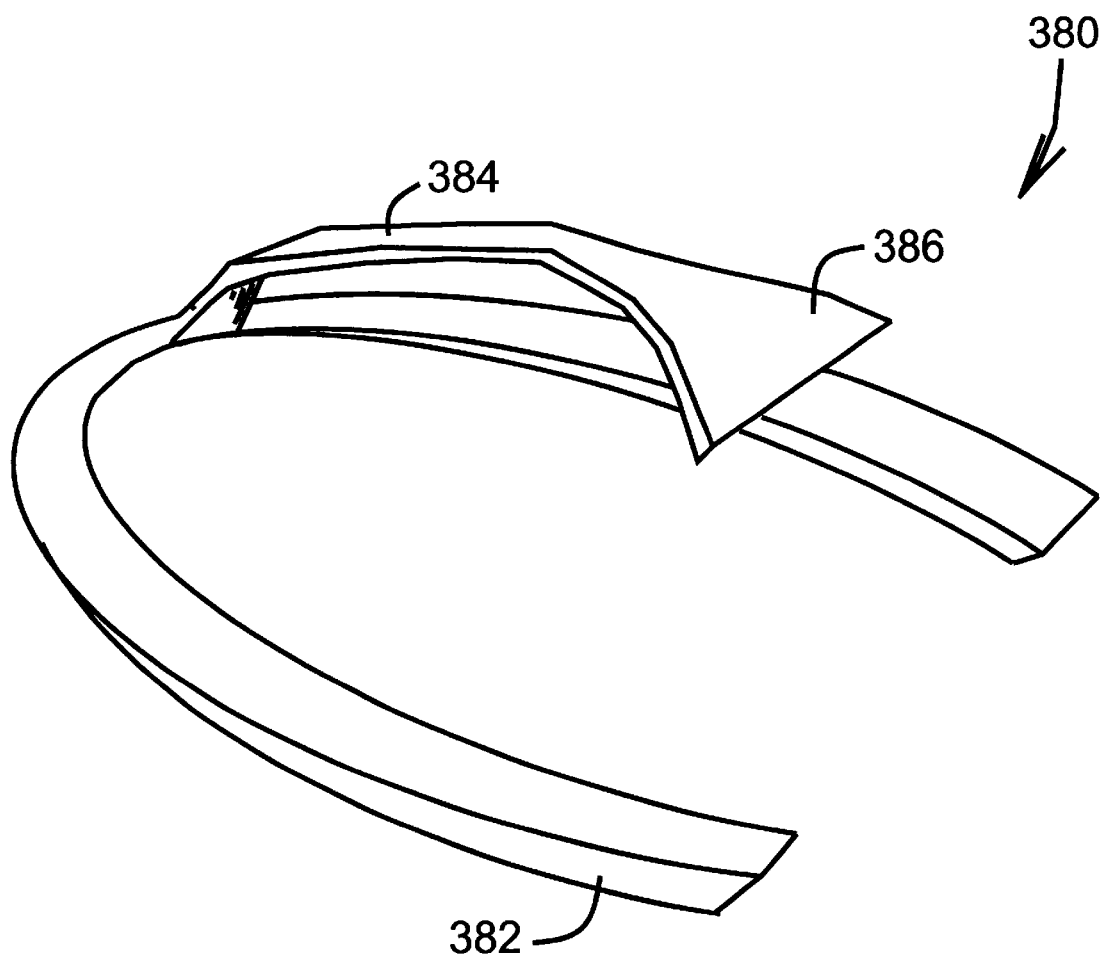
FIG. 19 is a single bottom strap and single top strap tapered from front to back to form a solid, broad top connector.
Figure 20:
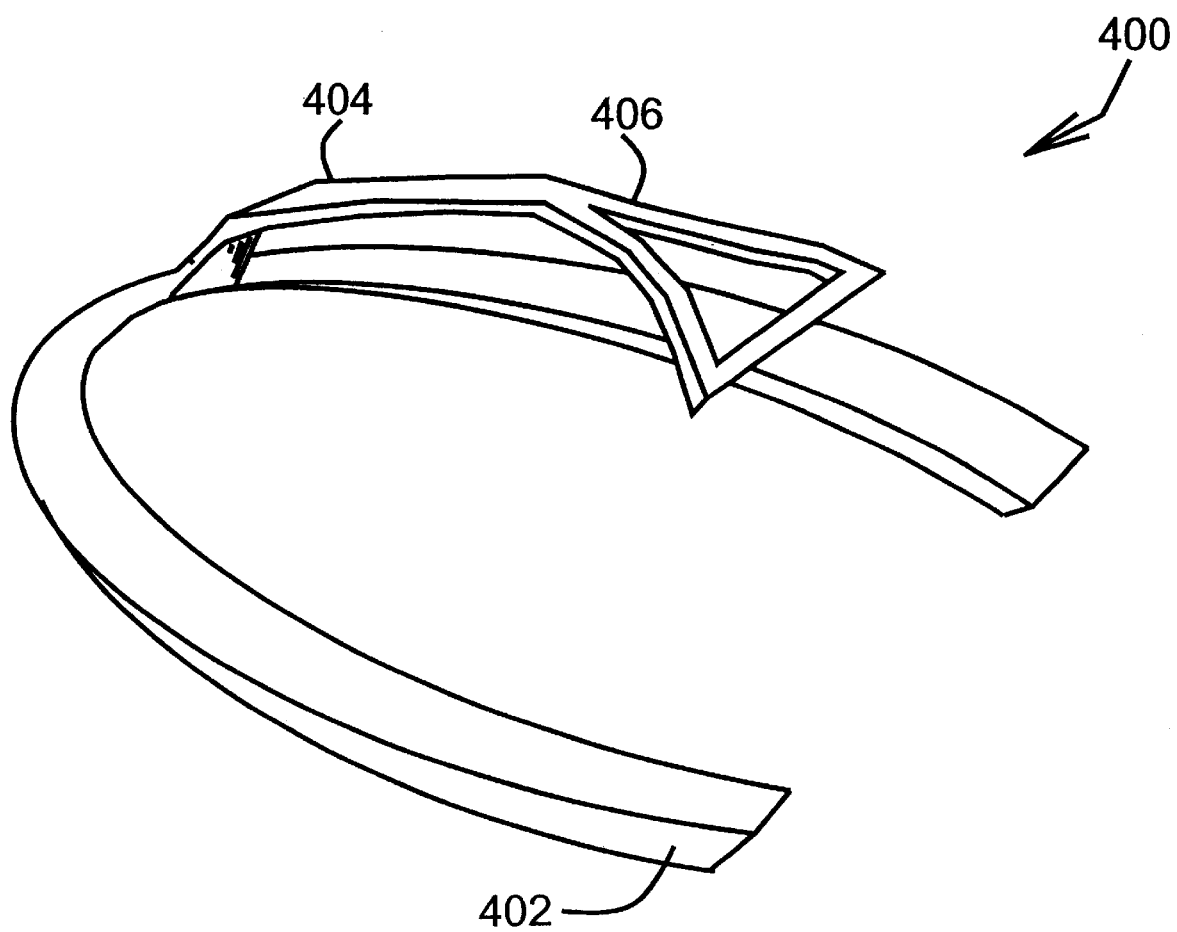
FIG. 20 is a single bottom strap and single top strap from front to back to form an open, broad top connector.
Figure 21:
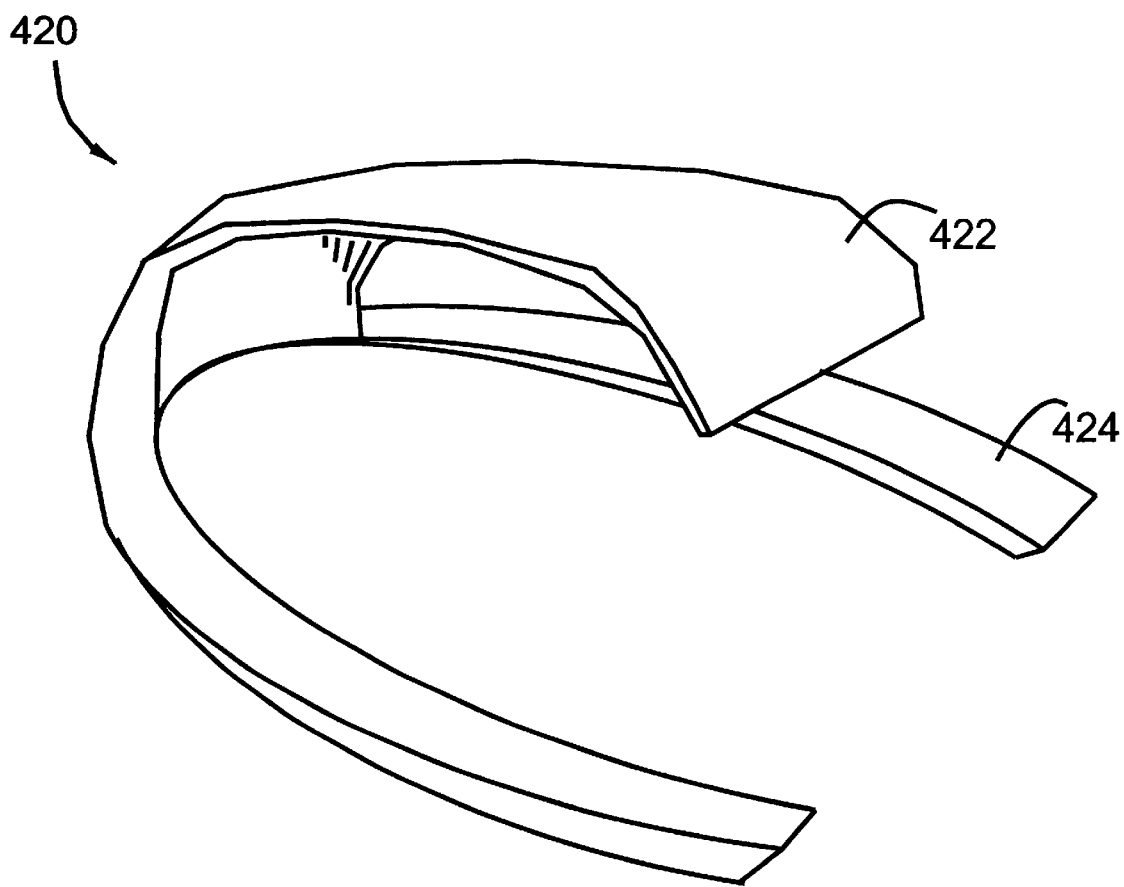
FIG. 21 is a perspective view of a wide top strap having a single bottom strap.
Figure 22:
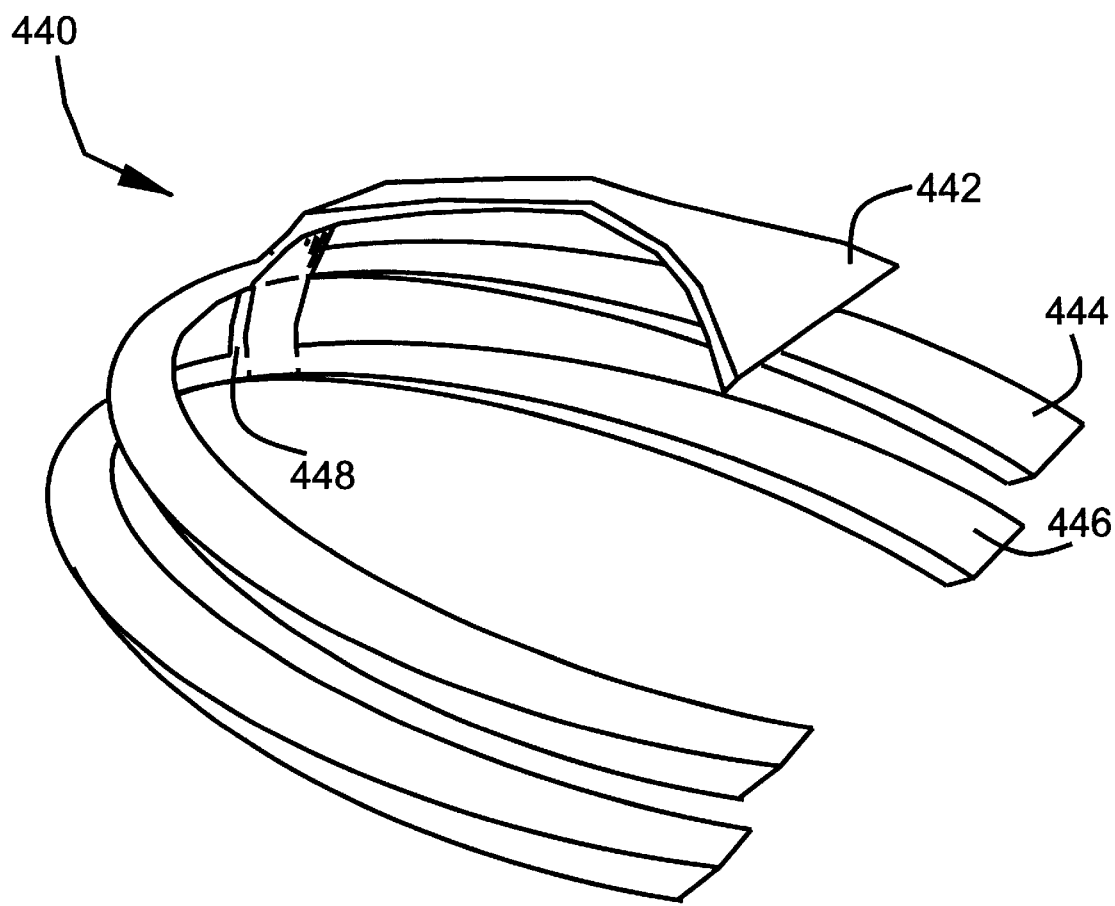
FIG. 22 is a perspective view of a tapered, wide top strap connected to lateral and bottom straps.
Figure 23:
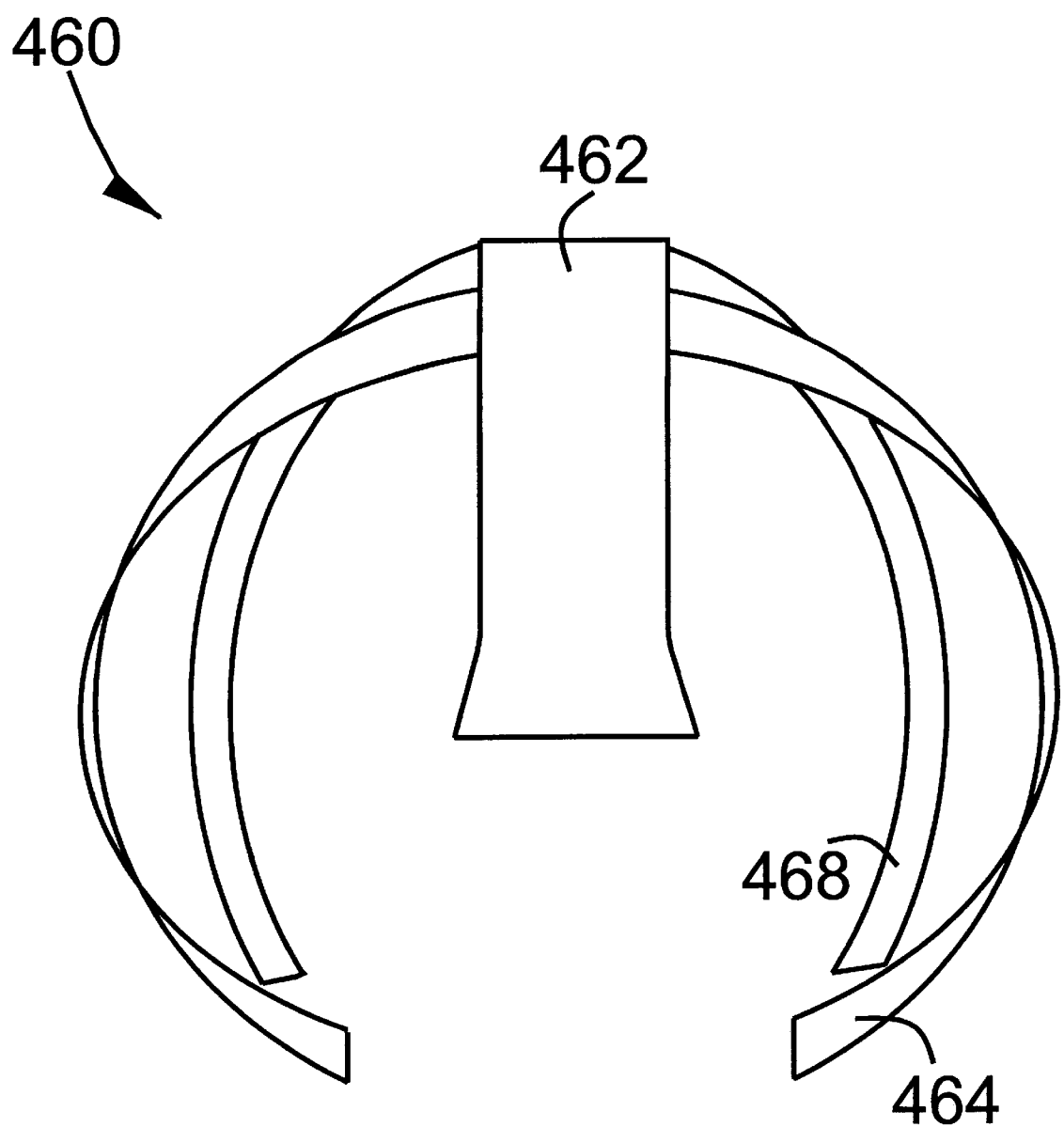
FIG. 23 is a top view of a non-tapered, wide top strap connected to lateral and bottom straps.

In FIGS. 16, 17, and 18 additional embodiment of the interface are illustrated as examples. In FIG. 16, the X-strap 340 is provided with a square interface 342. In FIG. 17 the X-strap 350 has crossing straps 352 and 356 and lateral strap 354 maintained in position through use of the interface 358. In FIG. 18, the round interface 362 is shown with crossing straps 364 and 368 and lateral strap 366. Additionally a center top strap 370 is added which serves to secure the larger goggles as described heretofore. In FIG. 19 the goggles strap 380 the individual top straps have been substituted with a solid, broad top connector 386. The broad top connector 386 is a modified triangle and connects to the top of the goggles, which is connected to the bottom strap 382 through the connector 384. In FIG. 20, the broad top 406 of the goggles strap 400 is an open triangle that is connected to the bottom strap 402 through use of a connector 404. In FIG. 21 the top connector 422 extends directly to the bottom strap 424 without any substantial change in width. In FIG. 22 the strap 440 also utilizes the wide top strap 422 in conjunction with a lateral strap 444 and bottom strap 446. A connector 448 connects the lateral strap 444 and the bottom strap 446. The wide top strap 442 of FIG. 22 tapers as it approaches the lateral strap 444. In FIG. 23, the wide, top strap 462 remains the same width and serves to connect the lateral strap 464 and the bottom strap 468.

Figure 24:
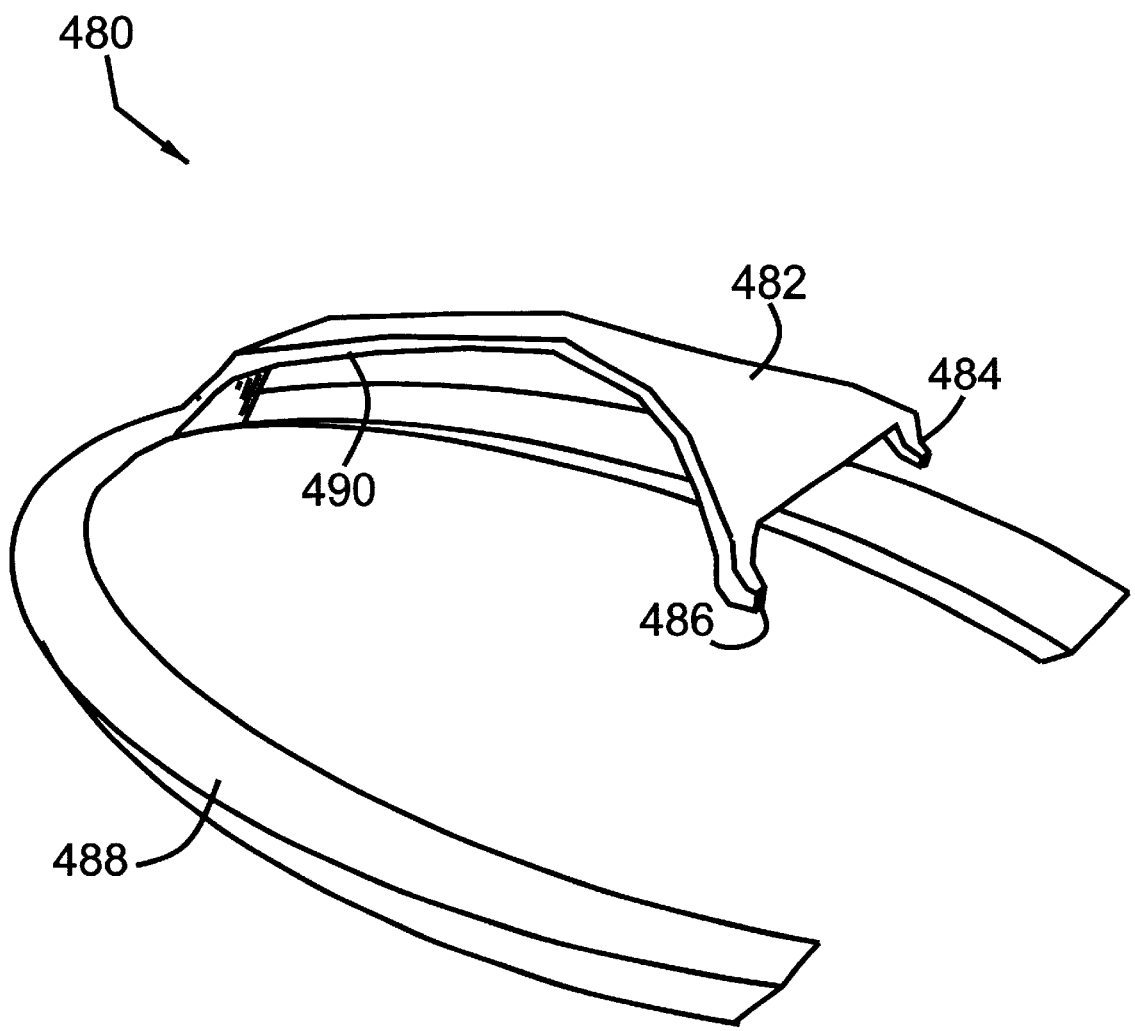
FIG. 24 is a perspective view of a wide top strap having flanges and connected to a single bottom strap.

In FIG. 24 the goggles strap 480 is provided with a tapering top strap 482 which is provided with connecting flanges 484 and 486 to permit the strap 460 to be connected to goggles having loop connectors, as illustrated in FIGS. 1–3. The top strap 482 is connected directly to the bottom strap 488. The strap 480 can, if desired, contain a second connection strap 490.

Figure 25:
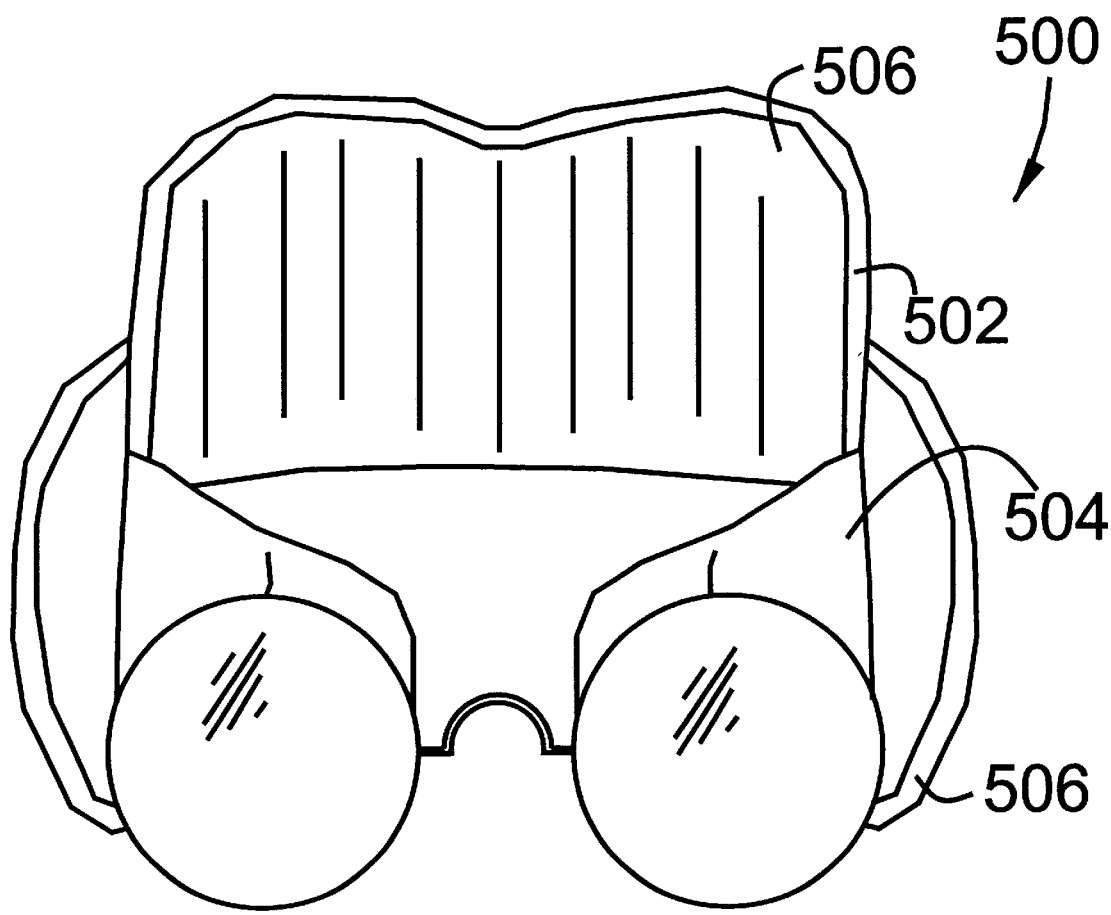
FIG. 25 is a front view of the goggles 504 containing a bottom strap 506 and a Lycra cap material between the straps.

FIG. 25 illustrates an embodiment that incorporates lycra cap material 506 between the top straps 502 and the bottom strap 506. This forms a bathing cap/goggles combination 500.

Figure 26:
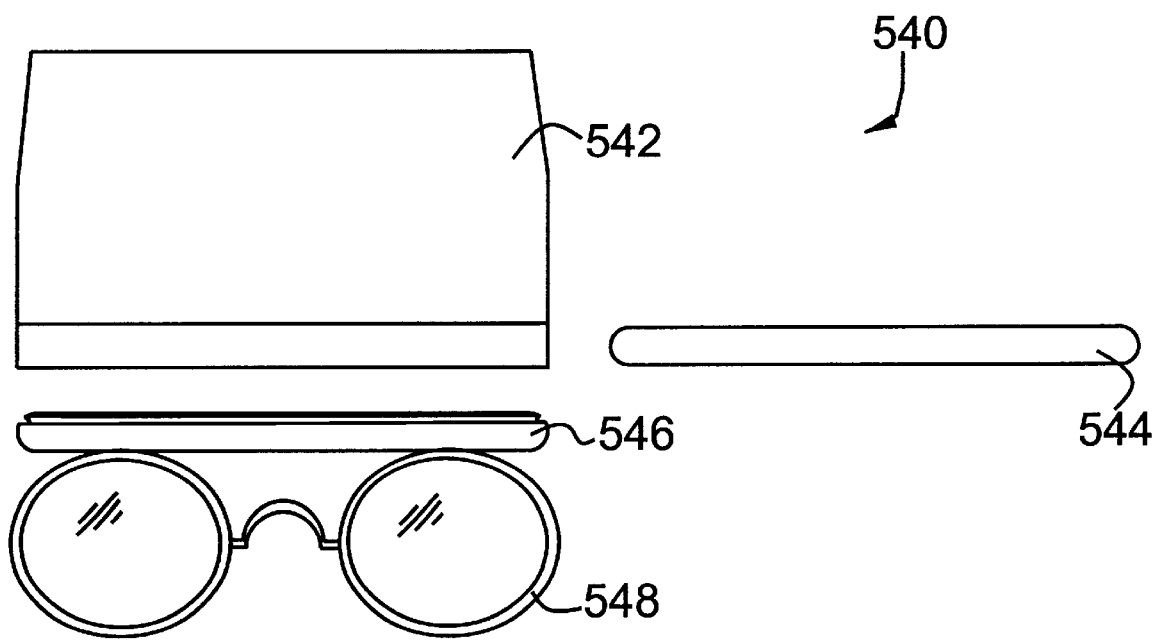
FIG. 26 is a front view of a groove like attachment means for the wide top straps.

FIG. 26 illustrates a replaceable goggles/strap combination 540 in which the strap 542 is removably attached to the goggles 548. The goggles 548 are provided with a receiving groove 546 that is dimensioned to receive the strap 542 and securing rod 544. The groove 546 is configured to retain the securing rod 544 and strap 542 securely and therefore must have a diameter only slightly greater than that of the securing rod 544. The goggle/strap combination 540 provides the advantage that the strap 542 can be replaced with any of the disclosed straps, depending upon use. Further, the goggles can be replaced if they become broken or an alternate style is desired.

Figure 27:
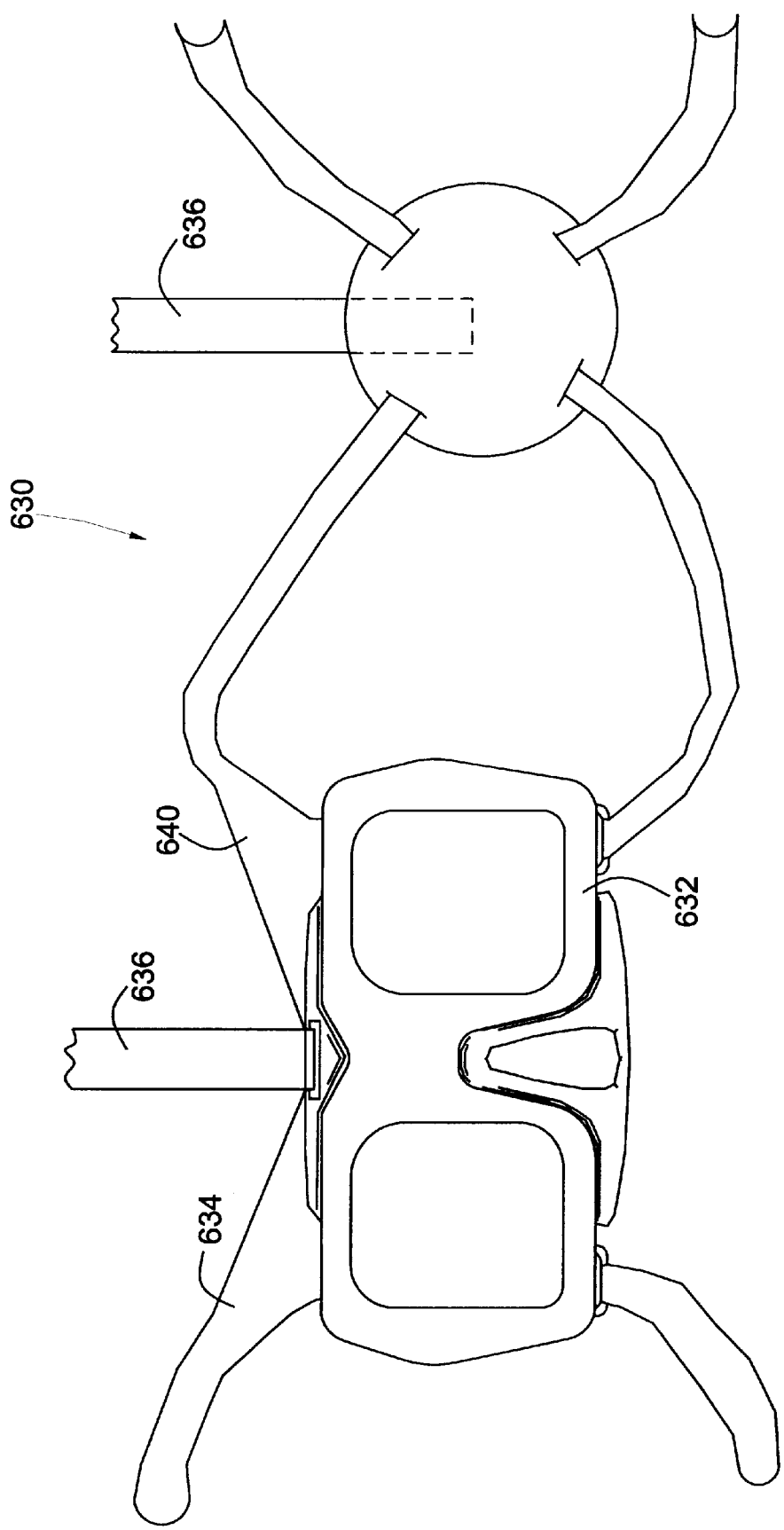
FIG. 27 is a broken view of an alternate embodiment of a divers mask using widened side straps.
Figure 28:
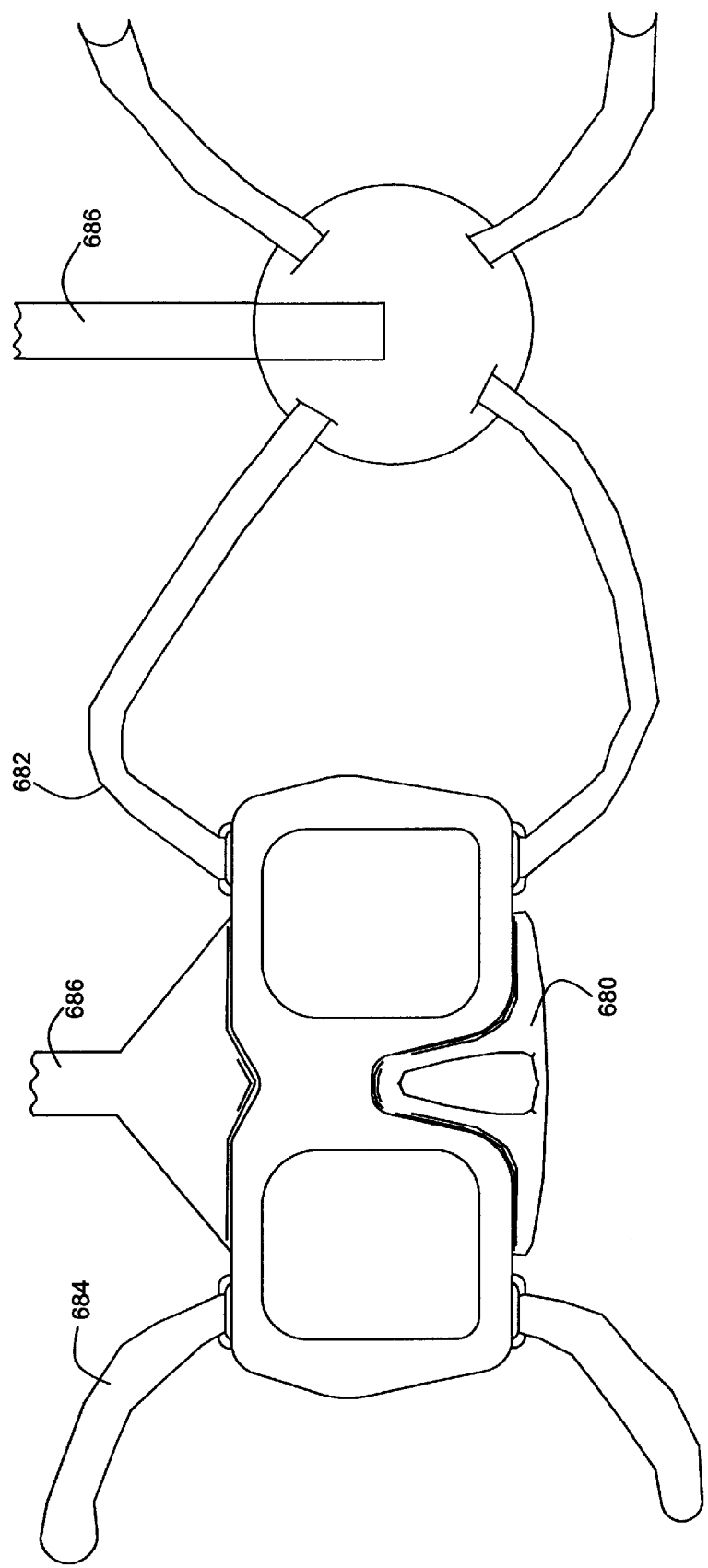
FIG. 28 is a broken view of an additional embodiment of a divers mask using a widened center strap.

In FIG. 27 the goggles assembly 630 reinforces the goggles 632 by widening the top of the straps 634 and 640 and attaching the wider area directly to the top of the goggles 632. An additional method for reinforcing the diving goggles is illustrated in FIG. 28 wherein goggles 680 are provided with a wider center strap 686 that is molded with, or directly attached to, the goggles 680. In this embodiment the crossed straps 684 and 682 maintain the narrow configuration. The diving goggles as illustrated in FIGS. 3, 27 and 28 are heavier than standard swimming goggles and tend to benefit from the heavier strap support. As with all of the foregoing embodiments, the straps can be either molded as part of the goggles or added after molding. Additionally, the straps can either be sized or adjustable, again, dependent upon cost of manufacture.

Figure 30:
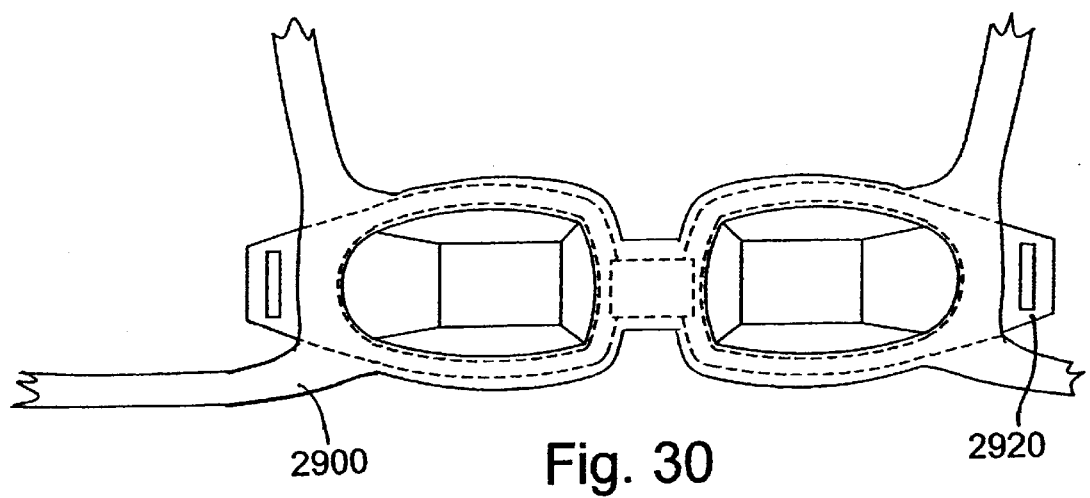
FIG. 30 is a fragmentary plan view of the overlay of FIG. 29 shown in position over a pair of goggles.
Figure 29:
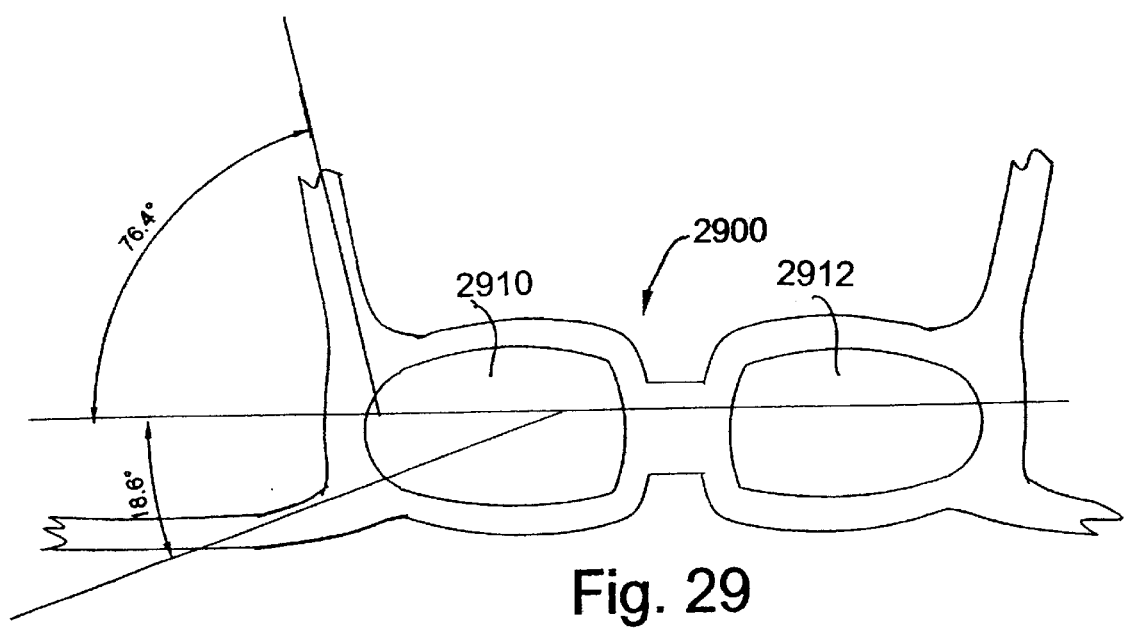
FIG. 29 is a fragmentary plan view of an overlay for use in retaining a pair of diving goggles in place.

The overlay of FIG. 29 provides a structure which is functionally equivalent to that of, for example, FIG. 1. The overlay indicated generally as 2900, has two holes 2910 and 2912 that are contoured to coincide with the perimeter configuration of the goggles 2920 of FIG. 30. The goggles 2920 is shown under the overlay 2900, partly in phantom where hidden by the overlay.

The foregoing straps are described for example purposes and other styles of straps will become apparent to those skilled in the art. Although the foregoing has been described in conjunction with swimming goggles, other goggles can be adapted.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed:

1. A modified sport or work goggles, comprising:
   a first and second top strap,
   a first and second bottom strap,
   a first and a second goggles lens, and
   a bridge,
   wherein the first and second goggles lenses are attached through the bridge and the first top and first bottom straps are opposedly attached to the first goggles lens and the second top and second bottom straps are opposedly attached to the second goggles lens.

2. The goggles according to claim 1, wherein the first and second top and bottom straps pass through four receiving slots in an interface member.

3. The goggles according to claim 2, wherein the first top and second bottom straps are one continuous strap and the second top and first bottom straps are one continuous strap.

4. The goggles according to claim 2, wherein the straps are non-continuous straps.

5. The goggles according to claim 4, wherein the straps are prevented from passing back through the interface by a securing means located on the side of the interface opposite said goggles lenses.

6. The goggles according to claim 1, wherein said top straps extend from said goggles at an angle in the range from about 35 to about 90 degrees relative to the longitudinal line of the goggles, and said bottom straps form an acute angle with respect to the longitudinal line of the goggles, in the range from about 15 to about 70°.

7. The goggles according to claim 6, wherein said top straps extend away from each other and form an angle relative to the longitudinal line of the goggles, in the range from about 45 to about 75° and said bottom straps are in the range from 20 to about 35°.

* * * * *